(12) United States Patent
Scheinberg et al.

(10) Patent No.: US 6,603,127 B1
(45) Date of Patent: Aug. 5, 2003

(54) BISMUTH-213 GENERATOR AND USES THEREOF

(75) Inventors: David Scheinberg, New York, NY (US); Ronald D. Finn, Rye, NY (US); Dangshe Ma, New York, NY (US); Michael R. McDevitt, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/647,491

(22) PCT Filed: Mar. 30, 1999

(86) PCT No.: PCT/US99/06955
§ 371 (c)(1),
(2), (4) Date: Dec. 19, 2000

(87) PCT Pub. No.: WO99/49931
PCT Pub. Date: Oct. 7, 1999

Related U.S. Application Data

(60) Provisional application No. 60/079,902, filed on Mar. 30, 1998.

(51) Int. Cl.⁷ .............................................. C01G 29/00
(52) U.S. Cl. ........................ 250/432 PD; 423/2; 423/6; 423/87; 423/249; 210/682; 424/1.11; 252/645
(58) Field of Search ...................... 250/432 PD; 423/2, 423/6, 87, 249; 210/682; 424/1.11; 252/645

(56) References Cited

U.S. PATENT DOCUMENTS 5,854,968 A * 12/1998 Horwitz et al. ....... 250/432 PD

* cited by examiner

*Primary Examiner*—Jack Berman
(74) *Attorney, Agent, or Firm*—Benjamin Aaron Adler

(57) ABSTRACT

The present invention provides a generator capable of producing therapeutic Bismuth-213 doses. Also disclosed are methods of preparing Bismuth-213-labeled compounds using such generator and applications of the labeled compounds.

38 Claims, 10 Drawing Sheets

BISMUTH-213 GENERATOR AND USES THEREOF

This application claims the benefit of U.S. Provisional Patent Application No. 60/079,902 filed Mar. 30, 1998.

BACKGROUND OF THE INVENTION

1. Field of the Invention

The present invention relates generally to the field of radioimmunotherapy. More specifically, the present invention relates to a Bismuth-213 generator and clinical uses thereof.

2. Description of the Related Art

The therapeutic potential of the alpha-particle emitting radionuclide, $^{213}$Bi, in the treatment of single cell neoplastic disorders such as leukemias (Nikula et al., 1998 and Jurcic et al., 1997), lymphomas, and micrometastatic neoplasms (McDevitt et al., 1996) and possibly other cancers and diseases, gives the construction of a stable and reliable radionuclide generator a high priority. Bismuth-213 ($^{213}$Bi) is a daughter radionuclide of $^{225}$Ac and the decay cascade is shown in FIG. 1 (Chang, 1996). There are six predominant radionuclidic daughters of $^{225}$Ac which are produced in the cascade to stable $^{209}$Bi and for each $^{225}$Ac decay there are a number of alpha-particle and beta-particle disintegrations, all of rather high energy. The cumulative $^{225}$Ac dose to a small mass of a functionalized organic resin due to 25 mCi $^{225}$Ac is substantial and will rapidly cause complete generator failure to occur. Furthermore, the continuous generation of radical species on the resin and in the generator eluate can lead to poor radiochemical labeling yields and poor recovery of labeled antibody product.

Currently published generator technology (Kaspersen et al., 1995 and Geerlings et al., 1993) is not adequate to prepare material for human use. In its published form, virtually no useable Bi-213 can be extracted from the generator when it is loaded with quantities of Ac-225 necessary to achieve human dose levels. This is because the concentrated Ac-225 damages the column material, causes breakdown and fusion of the column media, rapid leakage of Ac-225 from the column as well as leakage of other non-isotopic by-products, and ultimately prevents elution of the column or subsequent labeling reactions. Hence, a dose of Bi-213 suitable for human use could not be obtained from the generator described by Kaspersen or Geerlings (Kaspersen et al., 1995 and Geerlings et al., 1993) despite repeated attempts and the aforementioned problems were not anticipated based on their published methods.

The prior art is deficient in the lack of effective means of producing doses of Bi-213 suitable for clinical labeling for human use. The present invention fulfills this long-standing need and desire in the art.

SUMMARY OF THE INVENTION

The present invention is directed to a method for constructing and operating a $^{225}$Ac/$^{213}$Bi generator capable of producing 25–100 mCi of $^{213}$Bi suitable for clinical antibody labeling. The generator has been designed to have an effective lifetime of several weeks, producing up to six therapeutic doses of radionuclide per day. To date, 80 clinical doses have been prepared and injected into patients using the described $^{213}$Bi generator.

The present invention is also directed to methods of preparing $^{213}$Bi-labeled phamarceutical compounds using the $^{225}$Ac/$^{213}$Bi generator and related applications of these labeled compounds.

In one embodiment of the present invention, there is provided a Bi-213 generator comprising a first container containing $^{225}$Ac solution; a second container; a column; a third container; and a valve, wherein the valve connects the first container, second container and the column. Preferably, the Bi-213 generator is capable of producing from about 10 mCi to about 100 mCi of Bismuth-213 radionuclide.

In another embodiment of the present invention, there is provided a method for preparing a Bismuth-213-labeled compound, comprising the steps of: (a) eluting the generator with an elution buffer to obtain an eluate; (b) adding to the eluate with the compound to be labeled for reacting; (c) adding a quench solution to the reaction; and (d) purifying the solution from (c) to obtain a final product, which contains Bismuth-213-labeled compound. Preferably, the processing time for completing all the steps is from about 10 minutes to about 25 minutes. Representative bismuth-213-labeled compound include an antibody, a fragment of an antibody, a cytokine and a receptor ligand.

In still another embodiment of the present invention, there is provided a system for preparing a Bismuth-213-labeled compound, comprising a first container; the Bi-213 generator; a reaction vial; a second container; a column (or a filter); and a third container to collect final product, which contains Bismuth-213-labeled compound.

In still yet another embodiment of the present invention, there is provided a kit for preparing a Bismuth-213-labeled compound based on the above disclosed system.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
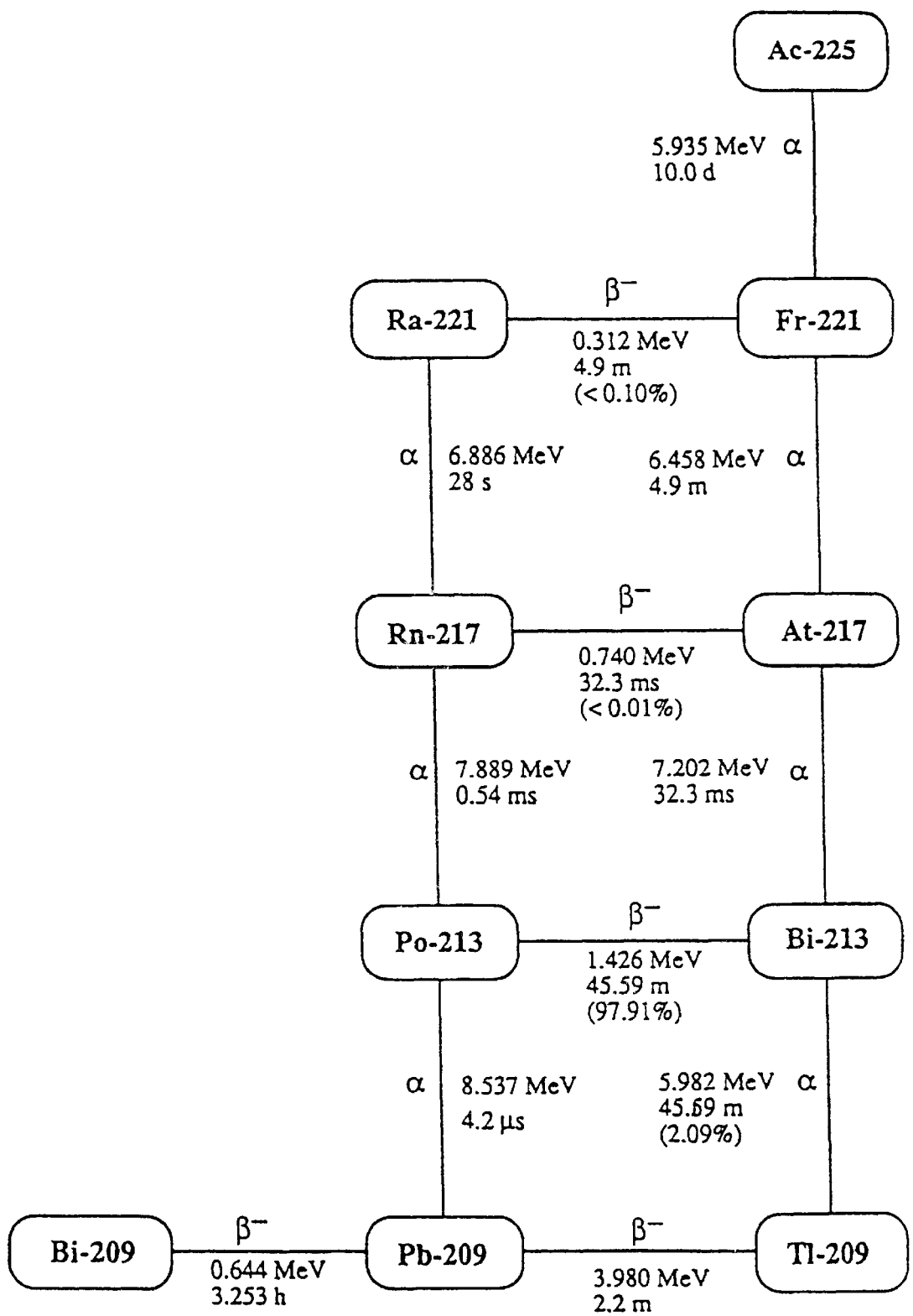
FIG. 1 shows the Ac-225 decay cascade with associated particulate decays and half-lives.

As used herein, the term "$^{213}$Bi generator" shall refer to a device used to prepare Bismuth atoms in pure form for therapeutic uses.

As used herein, the term "catch plug" shall refer to a part of the generator, comprised of resin, used to prevent elution of resin breakdown products and parent radionuclides.

As used herein, the term "porous polyethylene frits" shall refer to plastic filters that retain resin in the generator.

As used herein, the term "barbed reducing fittings" shall refer to plastic connectors used to attach tubing to the generator.

As used herein, the term "alpha particle emitting" shall refer to atoms that are radioactive and emit radiations comprising alpha particle.

As used herein, the term "beta particle emitting" shall refer to atoms that are radioactive and emit radiations comprising beta particles (electrons).

As used herein, the term "therapeutic dose" shall refer to a dose of drug emitting radiation between 1 mCi and 100 mCi.

As used herein, the term "effective lifetime" shall refer to the period of time that the generator is able to yield pure, reactive Bismuth-213.

As used herein, the term "radionuclidic purity" shall refer to the percentage of Bismuth-213 relative to other radionuclides (e.g. Ac-225).

As used herein, the term "iodide eluate chemistry" shall refer to the chemistry of I$^-$ and its various oxidation/reduction species with Bismuth-213 that cause the Bismuth-213 to elute from the generator and further react with chelate.

As used herein, the term "antioxidant" shall refer to a chemical that reduces the quantity of damaging oxidizing elements within a solution or device.

As used herein, the term "quench solution" shall refer to a chelate species to separate any unreacted Bismuth-213 and facilitate purifications.

As used herein, the term "size exclusion purification" shall refer to the use of a molecular sieve resin to separate molecules based on their weights (or sizes).

As used herein, the term "anion exchange purification" shall refer to the use of resin to separate molecules based on their electric charge.

The present invention describes a radionuclide Bi-213 generator and the method for construction and operation of the radionuclide generator capable of initially producing 10–200 mCi of Bi-213 (from Actinium-225) suitable for ligand or antibody labeling. Such ligands or antibodies are useful for therapy of cancers and other diseases where a pathological cell must be selectively killed. The generator has an effective lifetime of several weeks, producing up to six therapeutic doses of isotope per day, the limiting factor being the Ac-225 activity level. Factors such as radiation damage to the generator, metal-ion contamination, Ac-225 breakthrough, and isotope dilution that had previously limited feasibility of this approach were addressed and the improvements were made to overcome these problems described. Successful clinical use of the product in humans was described as an example.

The present invention is directed to a generator for producing clinically usable Bi-213 for labeling. There are four significant changes to the method, providing significant advances: 1) the Ac-225 is distributed within the entire column matrix, thereby reducing local radiation dose. As a consequence, destruction and fusion of the column does not occur; 2) Washing of the column is performed so as to not allow buildup of species that damage the column and prevent labeling and buildup of byproducts; 3) Anti-oxidants were added to the bismuth product before adding the reaction mixture, to decrease radiolytic damage to the antibody or other suitable carrier ligand; and 4) Catch plugs (guards) to prevent Ac-225 leakage were added. As disclosed herein, the use of catch plugs on the generator of the present invention and the use of radiation (free radical scavengers) to protect column and drug are significant.

The present invention is also directed to methods of preparing Bi-213-labeled phamarceutical compounds for therapeutic uses.

In one embodiment of the present invention, there is provided a Bi-213 generator comprising a first container containing $^{225}$Ac solution; a second container; a column; a third container; and a valve, wherein the valve connects the first container, second container and the column. The Bi-213 generator is capable of producing from about 10 mCi to about 100 mCi of Bismuth-213 radionuclide. Preferably, the container is a syringe, or a suitable reservoir, or a delivery device. The valve is a 3-way stopcock. Still preferably, the second container contains a chromatographic medium and the third container applies a negative pressure for loading the medium onto the column. Specifically, the chromatographic medium is resin.

In another embodiment of the present invention, there is provided a method for preparing a Bismuth-213-labeled compound, comprising the steps of: (a) eluting the generator with an elution buffer to obtain an eluate; (b) adding to the eluate with the compound to be labeled for reacting; (c) adding a quench solution to the reaction; and (d) purifying the solution from (c) to obtain a final product, which contains Bismuth-213-labeled compound. Generally, the processing time for completing all the steps is from about 10 minutes to about 30 minutes and the compound reacts with $^{213}$Bi eluate at a temperature equal to or higher than room temperature. Preferably, the compound is selected from the group consisting of an antibody, a fragment of an antibody, a cytokine and a receptor ligand.

In one embodiment, the elution buffer is selected from the group consisting of NaI/HCl solution and NaBr/HCl solution. Further, it is preferable that the elution buffer is mixed with an antioxidant, such as l-ascorbic acid.

In another embodiment, the compound to be labeled is premixed with an neutralizing buffer selected from the group consisting of $NH_4Ac$, Na citrate and $NH_4$ citrate.

In still another embodiment, the quench solution is selected from the group consisting of EDTA, DTPA, EDTMP, EDTA+HSA, DTPA+HSA, EDTMP+HSA and a chelate.

In yet another embodiment, the purification method is selected from the group consisting of size exclusion chromatography, anion exchange purification, reverse phase chromatography and affinity chromatography.

In still another embodiment of the present invention, there is provided a system for preparing a Bismuth-213-labeled compound, comprising a first container; the Bi-213 generator; a reaction vial; a second container; a column (or a filter); and a third container to collect final product, which contains Bismuth-213-labeled compound. Preferably, the system further comprises a cartridge appended to the exit end of the generator to reduce the leakage of $^{225}Ac$. In one preferred embodiment, the first syringe contains an elution buffer selected from the group consisting of NaI/HCl solution and NaBr/HCl solution. Further preferably, the elution buffer is mixed with an antioxidant, such as l-ascorbic acid. In this embodiment, the compound to be labeled is premixed with an neutralizing buffer selected from the group consisting of $NH_4Ac$, Na citrate and $NH_4$ citrate. The quench solution may be EDTA, DTPA, EDTMP, EDTA+HSA, DTPA+HSA, EDTMP+HSA and a chelate. Representative purification methods include size exclusion chromatography, anion exchange purification, reverse phase chromatography and affinity chromatography.

In still yet another embodiment of the present invention, there is provided a kit for preparing a Bismuth-213-labeled compound based on the above disclosed system.

The following examples are given for the purpose of illustrating various embodiments of the invention and are not meant to limit the present invention in any fashion.

EXAMPLE 1

Generator Construction

Bismuth-213 was produced from a "no carrier added" $^{225}Ac$ source (Van Geel et al., 1994; Van Geel, 1995; Boll et al., 1997) provided as the nitrate from the Institute for Transuranium Elements (Karlsruhe, Germany) or Oak Ridge National Laboratory (Oak Ridge, Tenn.). The $^{225}Ac$ was bound to an AGMP-50 cation exchange resin (Geerlings et al., 1993) utilizing modifications (McDevitt et al., 1996 and Finn et al., 1997) that allow the generator to yield the maximum recoverable amount of $^{213}Bi$ every 5 hours (secular equilibrium is established) over a period of several weeks.

Approximately 20–28 mCi of $^{225}Ac$ residue was received dry inside a quartz ampoule which was attached with 1/32 inch diameter tubing to a 5.5 cm×0.64 cm column of inert fluoropolymer tubing (i.d. 0.40 cm) with barbed reducing fittings, porous polyethylene plugs (0.16 cm thick), acid washed quartz glass wool, and approximately 220 mg of dry AGMP-50 resin, 100–200 mesh, $H^+$ form (BioRad Laboratories, Hercules, Calif.). The ampoule and column were initially disconnected, and the ampoule fitted with two 3-way stopcocks. The residue in the quartz ampoule was digested with 0.5 ml of 3 M Optima grade HCl (Fisher Scientific), added through one of the stopcocks. The other end of the quartz ampoule containing the $^{225}Ac$ acid solution was opened to a second syringe allowing release of any pressure increase due to heat or gas generation. The 3 M acid was allowed to contact the residue in the quartz ampoule for 0.5 hour with mild agitation to completely dissolve all of the $^{225}Ac$. After 0.5 hour the syringe used to apply the 3 M HCl solution was exchanged for a syringe containing 0.5 ml of metal-free water and the acidic actinium chloride solution then diluted to yield a 1.5 M HCl solution. The resulting acidic solution of actinium was withdrawn into a 5 ml syringe, the ampoule washed once with 1 ml 1.5 M HCl and the wash combined with the $^{225}Ac$ solution. The ampoule and syringe are disconnected and the syringe 3 with the $^{225}Ac$ solution attached to the apparatus 1 depicted in FIG. 2.

While the $^{225}Ac$ residue was being dissolved in the HCl the resin in the column 4 provided was washed and equilibrated with 10 ml of 1.5 M Optima grade HCl. The barbed fitting and the quartz wool on one end of the column 4 was then carefully removed and approximately 210 mg of the resin was removed by backwashing into a clean plastic dish with a solution of 1.5 M HCl and approximately 200 mg of the removed resin was placed into a clean 10 ml syringe 2 in 2 ml of 1.5 M Optima grade HCl solution. The 10 mg of washed resin remaining in the column 4 was fixed in place with a small piece of acid washed quartz glass wool and will serve as a "catch plug" while the other 10 mg of resin that was set aside will eventually be loaded back in the column 4 and serve as second "catch plug". These 10 mg sections of resin will serve as resin barriers to potentially capture $^{225}Ac$ that might break through during routine elution. A larger independent "catch plug", consisting of approximately 100 mg of AGMP-50 resin, placed inside a column with porous polyethylene frits and barbed reducing fittings, was later appended to the exit end of the generator to further reduce $^{225}Ac$ breakthrough during routine operation.

Figure 2:
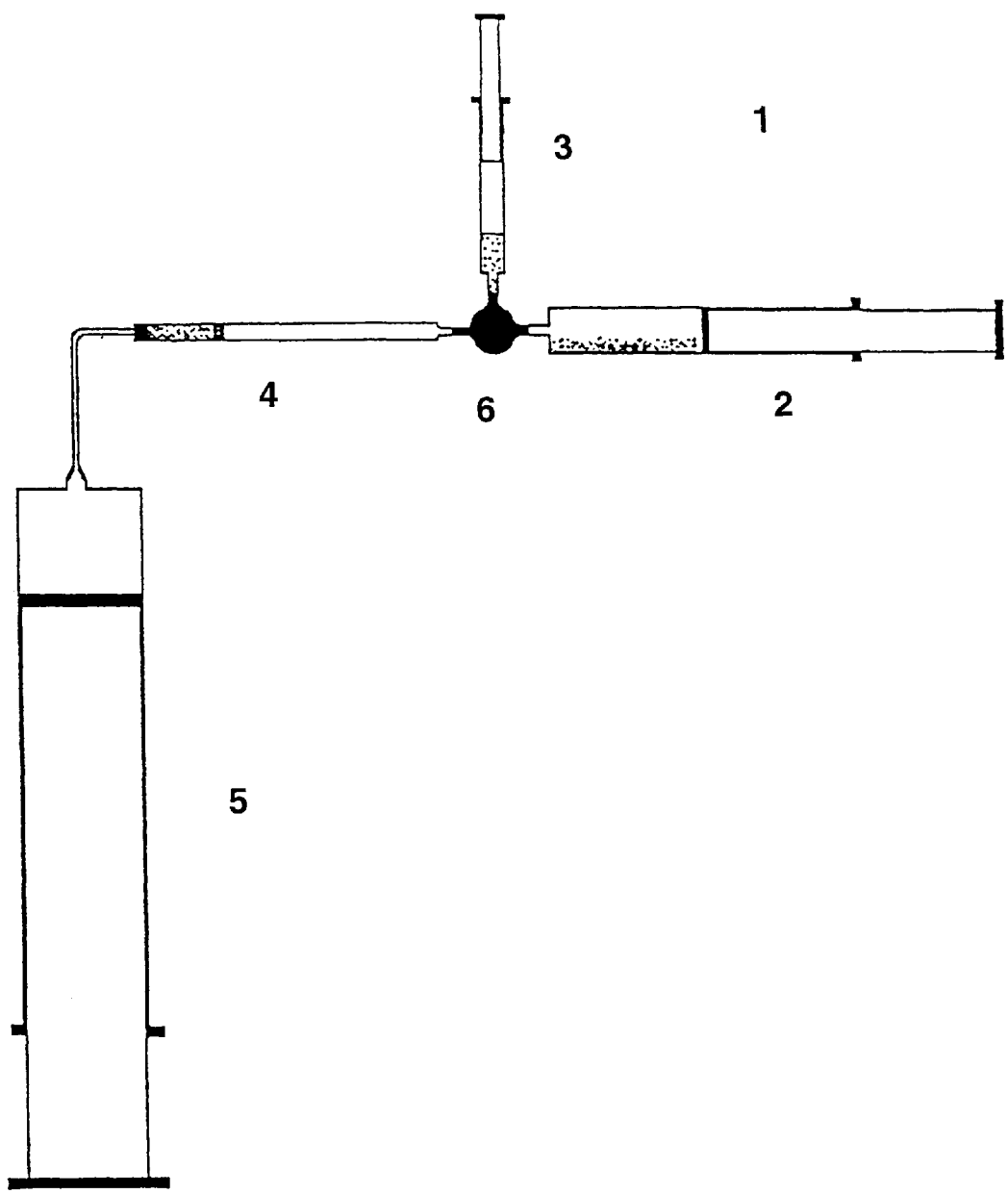
FIG. 2 shows the apparatus 1 for constructing the $^{213}$Bi generator, comprising a syringe 2 containing 1.5 M HCl equilibrated resin, a syringe 3 containing $^{225}$Ac/1.5 M HCl solution, a generator column 4 with "catch plug", a syringe 5 to apply a negative pressure for loading the resin onto the column and a 3-way stopcock 6.

The partially assembled generator column 4, the syringe 3 with the $^{225}Ac$ solution, and the 10 ml syringe 2 containing the 200 mg of the removed resin in 2 ml of 1.5 M Optima grade HCl solution were all attached via a 3-way plastic stopcock 6. The exit end of the column was attached to a 60 ml syringe 5 which was used to apply a negative pressure while filling the column 4. FIG. 2 illustrates the loading apparatus 1 configured with all pieces in place.

Manipulation of the 3-way stopcock allows the acidic $^{225}Ac$ solution to be pulled into the syringe containing the acidic AGMP-50 resin slurry. This $^{225}Ac$ solution and resin slurry are allowed to contact for 30 min with occasional gentle agitation. After batch loading the $^{225}Ac$ onto the resin support, the 3-way stopcock was again manipulated to load the $^{225}Ac$/resin into the column. Loading was accomplished by positioning the apparatus so that the column now stands vertically to allow the $^{225}Ac$/resin to flow downward. The resin was gently slurried prior to pulling it out of the 10 ml syringe with a slight negative pressure to pack the column. The stopcock position originally used for the syringe 3 with the $^{225}Ac$ solution was now attached to a clean syringe 2 with 10 ml of 1.5 M Optima grade HCl washing solution. This washing solution was pulled up into the 10 ml syringe (used to batch load the resin), agitated slightly to rinse the syringe, and then added to the generator column. The 60 ml syringe 5 was used to collect the wash solution passing through the column 4. The column 4 was disconnected from the 3-way stopcock 6 and a small plug of acid washed quartz wool was applied on top of the actinium loaded resin, followed by the remaining small 10 mg "catch plug" of AGMP-50 resin and another small plug of acid washed quartz wool. A barbed reducing fitting was attached and the generator was ready to use. It is recommended to position the generator vertically during operation so that any fines produced would settle out and not embed into the polyethylene frits. The generator was then washed with 2 ml of 1 mM metal-free HCl solution.

Actinium-225 activity received as a residue in a v-vial was dissolved in 3 M HCl, allowed to digest, diluted with metal-free water, and batch loaded onto 1.5 M HCl equilibrated AGMP-50 and a generator constructed in the manner as described above. Metal-free reagents, plasticware, and apparatus were employed to construct and assemble the generator in order to minimize the introduction of trace metals. The described method allows the $^{225}$Ac activity to be handled in essentially a closed system under controlled conditions.

EXAMPLE 2

Radionuclide Detection and Quantification

Bismuth-213 activity was routinely measured with a Squibb CRC-17 Radioisotope Calibrator (or equivalent model) (E.R. Squibb and Sons, Inc., Princeton, N.J.) set at 775 and multiplying the displayed activity value by 10. The activity value reported using the CRC calibrator was verified by counting a 0.005–0.020 ml (±0.00015 ml) sample aliquot point source taken from an accurately known volume (2 to 10 ml±0.02 ml) of generator eluate at a fixed geometry using a HPGe detector with pulse height multi-channel analysis (Canberra Industries, Meriden, Conn.). The HPGe detector counting efficiency of the $^{213}$Bi 440 KeV g-emission was determined for the same geometry from a plot of counting efficiency$^{-1}$ vs. the $\gamma$-energy of standard radionuclide sources. The radioisotope dose calibrator setting of 775 (multiplying the displayed activity value by 10) was selected based upon measurements taken from the pulse height multi-channel analyzed g-emission spectrum of a $^{213}$Bi sample. The $^{213}$Bi samples, ranging in volume from 0.05 to 10 ml, were positioned at the bottom and center of the well of the CRC-17 Radioisotope Calibrator.

Pulse height multi-channel analysis and gas ionization detection (Ambis 4000, Ambis Inc., San Diego, Calif.) were employed to determine the radionuclidic purity of the $^{213}$Bi eluate and of the purified radiolabeled antibody construct, [$^{213}$Bi]Bi-CHX-A-DTPA-HuM195, by looking for $^{225}$Ac breakthrough. An aliquot of the generator eluate and/or final product would be counted at least 75–100 hours post elution, allowing sufficient time for the original aliquot of $^{213}$Bi activity to decay and for the corresponding $^{209}$Pb activity (arising directly from the $^{213}$Bi aliquot) to also grow in and decay, leaving only the $^{225}$Ac breakthrough for measurement. If there was breakthrough of $^{225}$Ac and daughters in equilibrium into the sample, then it would generate $^{213}$Bi via secular equilibrium which could then be detected and quantified in these analyses. A standard curve was constructed for the $^{225}$Ac breakthrough analyses by spotting serial diluted amounts of $^{225}$Ac in 1 M HCl and counting these point sources on the Ambis 4000, using a standardized geometry, and counting the same sources on the multi-channel analyzer, using the 440 KeV $^{213}$Bi emission to back calculate the amount of $^{225}$Ac in equilibrium with the $^{213}$Bi. Selected samples containing $^{225}$Ac breakthrough were held and counted repeatedly over a several week period and the breakthrough activity decay values analyzed by curve fitting to determine the identity of the radionuclidic breakthrough.

After generator construction the dispersion of the $^{225}$Ac on the resin support was verified by placing a freshly (<1 minute) eluted and washed generator on a piece of Type 52, 4×5 sheet film (Polaroid, USA) for an appropriate length of time and developing (approx. 5 min. exposure for a 20 mCi generator). The exposed photographic image clearly shows the uniform dispersion of the radioactivity throughout the resin.

EXAMPLE 3

Generator Elution and Washing

Figure 3:
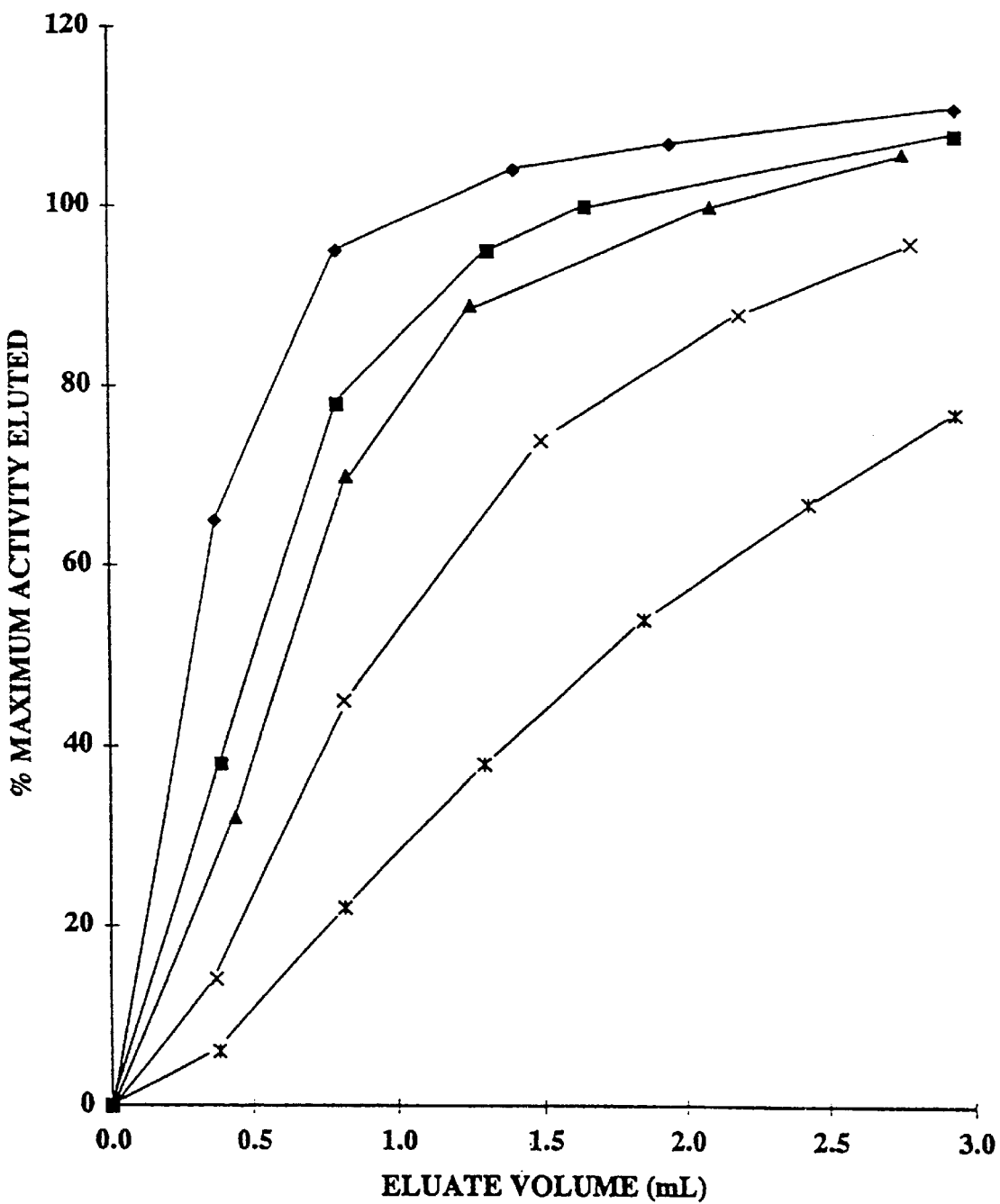
FIG. 3 shows the percent of total theoretical $^{213}$Bi eluted with varying iodide concentration: 0.10 M [I⁻]/0.10 M [Cl⁻] (diamonds); 0.05 M [I⁻]/0.15 M [Cl⁻] (squares); 0.04 M [I⁻]/0.16 M [Cl⁻] (triangles); 0.03 M [I⁻]/0.17 M [Cl⁻] (x); and 0.02 M [I⁻]/0.18 M [Cl⁻] (stars).

A 0.1 M HCl/0.1 M NaI solution (Atcher, 1988) was prepared fresh each time and used to elute $^{213}$Bi from the resin at a rate of approximately 1 ml/min. The $^{213}$Bi was eluted presumably as the (BiI$_5$)$^{2-}$ anion species (Spivakov, 1979) with 0.1 M HI. Varying the iodide concentration (FIG. 3) affects the elution characteristics of $^{213}$Bi species from the generator. The $^{213}$Bi reaches secular equilibrium with the $^{225}$Ac after approximately 300 min. (6.5 $^{213}$Bi $t_{1/2}$'s), however, after approximately 150 min. 90% of the maximum $^{213}$Bi activity is available for elution from the generator. Approximately 3 ml of 0.1 M HCl/0.1 M NaI solution was required to elute all of the recoverable $^{213}$Bi from the generator. The medium energy $^{213}$Bi 440 keV photon emission (28% abundance) was readily attenuated with a minimum amount of lead shielding and allowed for safe handling of multiple millicurie amounts of $^{213}$Bi in the labeling and purification steps. The generator was washed with 2 ml of 1 mM metal-free HCl solution following each elution. The first 0.5 ml of the wash solution can be added to the 3 ml of 0.1 M HCl/0.1 M NaI elution solution to augment the $^{213}$Bi yield.

EXAMPLE 4

Antibody Construct Radiolabeling and Purification

A freshly prepared 0.1 M HCl/0.1 M NaI solution was colorless, however after passage over the generator resin, it elutes as a yellow colored solution due to the production of I$_3^-$ ion. The $^{213}$Bi eluate was decolorized by the addition of enough demetalized l-ascorbic acid solution to produce a 5 g/l solution. The l-ascorbic acid also prevents significant loss of radiolabeled antibody during the purification over P6 gel (see below), acting as a radioprotecting agent. Addition of 0.25 ml of 3 M ammonium acetate was required to buffer 3 ml of 0.1 M HCl/0.1 M NaI $^{213}$Bi eluate to pH 4–5. Humanized monoclonal antibody (mAb) construct (0.3 to 0.5 mg), CHX-A-DTPA-HuM195 (TSI Washington Laboratories, Bethesda, Md.), was added to the buffered, radioprotected $^{213}$Bi solution and incubated at room temperature for up to 10 min. Following this incubation, 0.02 ml of 10 mM EDTA solution was added to quench the reaction mixture (i.e., chelate any remaining reactive $^{213}$Bi species).

The radiolabeled antibody was purified from the low molecular weight radioactive impurities, l-ascorbic acid, and other labeling reagents by using a 10DG desalting column containing P6 gel (BioRad Laboratories, Hercules, Calif.) as the stationary phase and using 1% HSA as the mobile phase. Collection of approximately 7.5 ml of column eluate yields the final formulated product and the purity is determined by ITLC-SG.

In conclusion, the labeling and purification procedure for the alpha emitting radiometal Bi-213 includes: elute generator with a freshly prepared 3 ml 0.1 N NaI/HCl solution; add 0.25 ml 3 N NH4Ac and check pH; add 0.1 ml 150 g/l l-ascorbic acid; add antibody and check pH; react for 8–10 minutes with gentle mixing at ambient temperature; add 20

μl of 10 mM EDTA quench solution; aliquot quality control sample; load onto prewash/equilibrated size exclusion purification column; elute with 10 ml of 1% HSA; collect fraction of elution; adjust antibody and HSA concentration to prepare patient dose and aliquot quality control samples from residual product.

EXAMPLE 5

$^{213}$Bi-Labeled Antibody Product Analyses

The observed radiolabeling reaction efficiency was determined by instant thin layer chromatography (ITLC-SG) using a 0.001 ml aliquot of the reaction mixture applied to silica gel impregnated paper (Gelman Science Inc., Ann Arbor, Mich.) (Nikula, 1995). The paper strips were developed using two different mobile phases. Mobile phase I was 10 mM EDTA and II was 9% NaCl/10 mM NaOH. The Rf of the radiolabeled antibody was 0 and both the free metal species and metal chelates have Rf of 1.0 in mobile phase I. In mobile phase II, the radiolabeled antibody and free metal species have Rf of ~0 and the metal chelates have Rf of 1.0. The strips were cut at Rf=0.5 and counted in a Packard Cobra g-counter (Packard Instrument Co., Inc., Meriden, Conn.) using a 340–540 KeV window or counted intact using a System 400 Imaging Scanner (Bioscan Inc., Washington, D.C.) or the Ambis 4000.

EXAMPLE 6

Immunoreactivity Determination

The viability of the purified $^{213}$Bi labeled antibody was ascertained by determining the immunoreactivity of the $^{213}$Bi labeled CHX-A-DTPA-HuM195 construct as described (Nikula et al., 1995) by incubating 2 ng of radiolabeled mAb in 0.030 ml total volume with a 20- to 30-fold excess of antigen ($10 \times 10^6$ CD33 positive AL67 or HL60 cells). These cells have approximately 10,000–20,000 CD33 positive binding sites per cell (Nikula et al., 1995) and have the capacity to bind up to 90% of added HuM195. After a 30 minute incubation at 0° C., the cells were collected by centrifugation and the supernatant containing unbound mAb was removed to a second set of cells and incubated (30 min.) with the same amount of excess antigen as in the first incubation at 0° C. Under these conditions of large antigen excess in a small volume, the reaction goes to near completion in 60 minutes. The percentage immunoreactivity was calculated as equal to (bound radiolabeled CHX-A-DTPA-HuM195 construct to cells #1 plus cells #2)/(total bound plus unbound radiolabeled CHX-A-DTPA-HuM195 construct) times 100. Specific binding in these assays was confirmed by lack of binding of the radiolabeled CHX-A-DTPA-HuM195 construct to CD33 negative RAJI or MOLT 4 cell lines. To avoid nonspecific and Fc receptor binding, the assays were performed in the presence of 2% human serum (Caron et al., 1992).

EXAMPLE 7

Iodide Ion Chemistry

The absorption spectra of 0.1 M HCl/0.1 M NaI solutions were obtained following i) prolonged air oxidation at ambient temperature; ii) oxidation by the action of 0.09% $H_2O_2$; and iii) elution through a $^{213}$Bi generator. These yellow colored solutions were decolorized upon adding an aliquot of l-ascorbic acid (5 mg/ml final [l-ascorbic acid]). All four of the solutions were initially 0.1 M HCl/0.11 M NaI and were diluted 100-fold for spectrophotometric measurement.

Results and Discussion

Previous attempts to load high levels of the acidic $^{225}$Ac chloride solution (15–25 mCi) directly onto a prewashed, prepacked column of AGMP-50 resin resulted in the $^{225}$Ac being deposited in a very small layer at the very top of the resin as confirmed by a 4×5 sheet film image of the generator. This method of loading resulted in the catastrophic failure of the generator within 1–2 days of construction. Generator failure was defined as excessive $^{225}$Ac breakthrough, catastrophic radiolytic damage to the resin (sintering) and to the plastic body of the column (cracking). The sintering of the resin results in the production of particulate fines which block the flow of solution through the generator. Generators constructed in this manner could not be used for clinical preparations of radiopharmaceuticals. The effects of radiation damage to ion exchange materials are well documented (Gangwer et al., 1977) and it was known that organic cation exchange resins are considerably degraded when the total absorbed doses are greater than $1 \times 10^8$ rads. The total energy emitted per decay of $^{225}$Ac is $4.493 \times 10^{-12}$ J (28.08 MeV).

Figure 4:
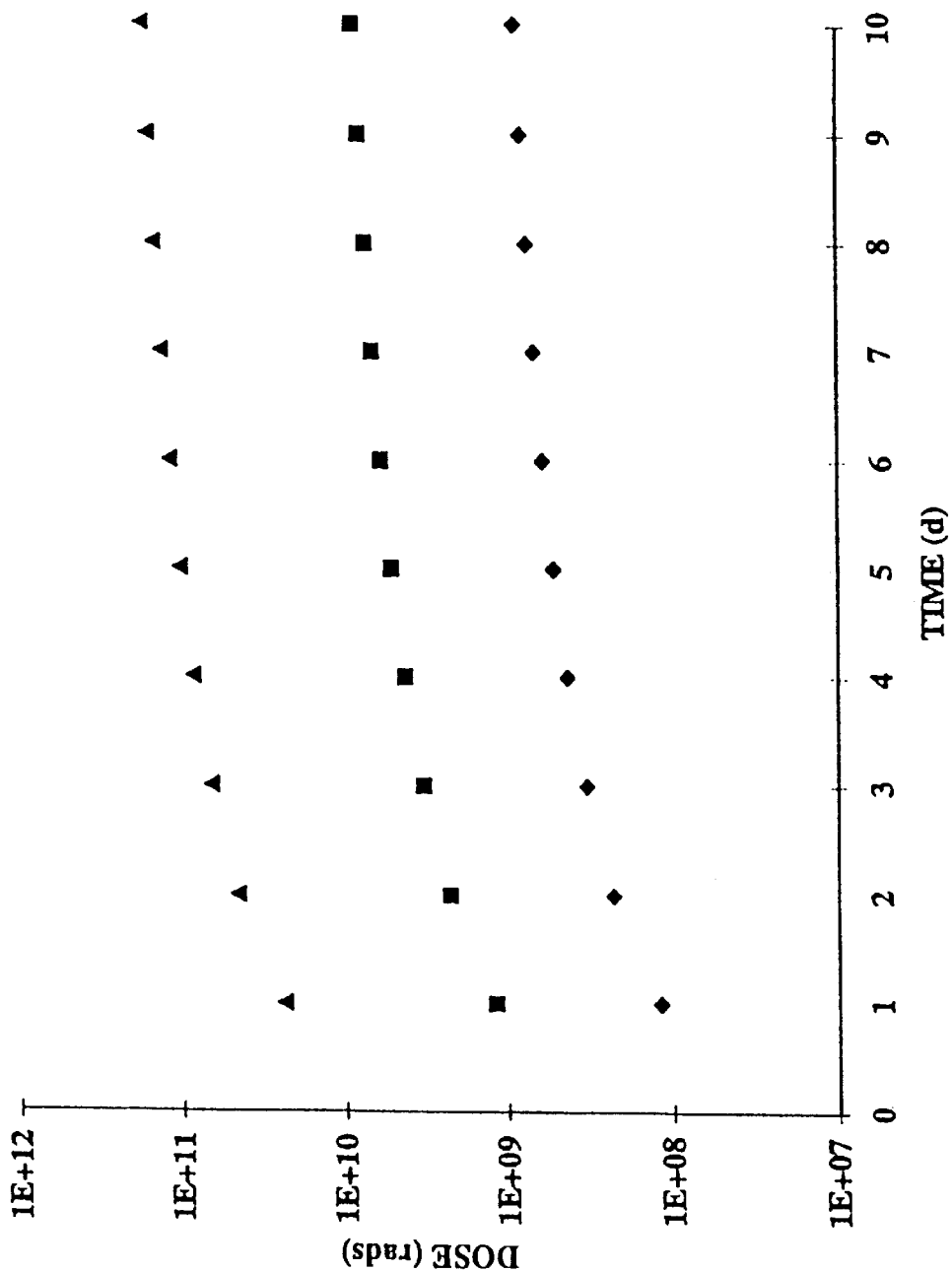
FIG. 4 shows log of the dose from 25 mCi $^{225}$Ac to 200 (diamonds), 20 (squares), and 1 (triangles) mg of resin vs. time.

The radiation dose to the AGMP-50 resin due to $^{225}$Ac and the radionulidic daughters in its decay cascade is large because of the 10 day half-life of the parent radionuclide. In practice, 15–25 mCi of $^{225}$Ac loaded onto the small mass of resin (<2 mg) at the top of the column utilizing routine loading methods was observed to rapidly destroy the viability of the generator components and the resin material. Calculations of the dose from 25 mCi of $^{225}$Ac and the predominant daughter radionuclides to 200, 20, and 1 mg of resin confirm these observations and serve as a guide for successful generator construction. The results of such calculations are shown in FIG. 4 plotting the log of the $^{225}$Ac dose to varying amounts of resin vs. time. For example, over a 10 day period the dose to 1 mg of a polymeric cation exchange resin from 25 mCi of $^{225}$Ac is $1.8 \times 10^{11}$ rads while the dose from the same amount of activity dispersed over 200 mg of resin is $8.8 \times 10^8$ rads. These calculations demonstrate the necessity of loading the $^{225}$Ac over a large mass of resin, especially when the organic cation exchange resins are considerably degraded when exposed to total absorbed doses greater than $1 \times 10^8$ rads. Greater resistance to radiolytic damage would be imparted by using inorganic resin supports (Gangwer et al., 1977 and Wu et al., 1996), however, these materials may alter the reactivity of the generator eluate by the introduction of advantageous metal-ions or necessitate time consuming elution conditions.

A fundamental improvement that allows for clinical use of the generator is the uniform distribution of the $^{225}$Ac throughout the resin mass. Batch loading the $^{225}$Ac in the manner described above has resulted in a generator that will produce chemically reactive $^{213}$Bi for several weeks. The construction method described was used to prepare 12 clinical generators resulting in 94.2%±5.9% (n=12) of the total $^{225}$Ac activity received being loaded onto the AGMP-50 resin for clinical use; 3.1%±2.8% (n=12) of the $^{225}$Ac was lost in the resin loading syringe (residual particles); 2.3%±3.6% (n=12) remained in the quartz ampoule used for shipping; and 0.3%±0.2% (n=12) of the $^{225}$Ac activity was found in the collected 1.5 M HCl washes. These percentages were determined after $^{225}$Ac secular equilibrium was established and the $^{213}$Bi in the wash solutions was allowed to decay.

Gas ionization detection of the β- and γ-emissions in the $^{225}$Ac decay cascade was used to determine the level of $^{225}$Ac breakthrough above the $50 \times 10^{-12}$ Ci limit of detection. Pulse height multi-channel analyses of generator eluates and formulated products using a HPGe detector has a $20\times10^{-9}$ Ci limit of detection such that detection of the presence of $^{225}$Ac breakthrough in any of the aliquots was not seen. There was a low level of $^{225}$Ac breakthrough in the generator eluate which ranged from $2.0\times10^{-6}$/ml±$0.7\times10^{-6}$/ml (n=5) during week 2 to $5.7\times10^{-6}$/ml±$2.1\times10^{-6}$/ml (n=4) during week 3. The purification of the radiolabeling reaction mixture via size exclusion chromatography reduced the $^{225}$Ac breakthrough value to $0.29\pm10^{-6}$/ml±$0.11\pm10^{-6}$/ml (n=6). The $^{225}$Ac breakthrough is expressed as the nCi of $^{225}$Ac per ml of the eluate (or final product) per mCi of $^{225}$Ac on the generator.

The generator eluate $^{225}$Ac breakthrough value was significantly reduced to $0.13\times10^{-6}$/ml±$0.02\times10^{-6}$/ml (n=3) by the addition of an independent "catch plug" of 100 mg of AGMP-50 resin packed into a small column that was attached to the exit end of the generator. The most practical solution was to append this 100 mg "catch plug" at the exit end of the generator thus reducing the $^{225}$Ac breakthrough into the generator eluate prior to radiolabeling, and utilizing the size exclusion chromatography to further reduce $^{225}$Ac breakthrough value to $0.06\pm10^{-6}$/ml. Additionally, since the $^{225}$Ac breakthrough was primarily retained on the independent 100 mg "catch plug" of AGMP-50 and recovered, it proved to be a reasonable manner to manage the long-lived $^{225}$Ac contaminant.

Actinium-225 (and the daughters) was determined to be the radionuclide that was present in the breakthrough samples. Selected samples containing $^{225}$Ac/$^{213}$Bi generator breakthrough were held and counted repeatedly over a several week period. The breakthrough activity decay values were analyzed by curve fitting routines and found to fit an $^{225}$Ac decay curve.

A second improvement that allows clinical applications of this method is the addition of l-ascorbic acid (reaction concentration of approximately 5 g/l) to prevent significant loss of radiolabeled antibody during the purification over P6 gel. This loss is presumably a consequence of protein denaturation. In the absence of this radioprotecting agent, recovery of [$^{213}$Bi]Bi-CHX-A-DTPA-HuM195 after passage over a 10DG desalting size exclusion column containing P6 gel was 47±25% (n=13) with a significant amount (22%±18% (n=13)) of radioactivity remaining on the column after sufficient washing. Addition of l-ascorbic acid to the reaction mixture (n=28) results in a 69%±6% recovery of [$^{213}$Bi]Bi-CHX-A-DTPA-HuM195 with only 1.5%±1.4% of radioactivity remaining on the column after washing. This agent significantly improves both the yield and reproducibility of the labeling and purification processes thus allowing production of clinically useful amounts of $^{213}$Bi. It is likely that other radioprotecting agents could be substituted for l-ascorbic acid.

The observed radiolabeling reaction efficiency was 78%±9% (n=57) as determined by ITLC-SG. Purification via size exclusion chromatography yields a product of 98%±2% purity (n=57) as determined by ITLC-SG. Total processing time (i.e., the time from the end of generator elution to formulation of product for injection) was 23 min.±3 min. (n=56). The specific activity of the [$^{213}$Bi]Bi-CHX-A-DTPA-HuM195 construct was 14.3 Ci/g±3.9 Ci/g (n=57). These radiolabeling, purification, and analytical conditions were applicable to all the other antibody constructs that were examined.

The labeling reaction was allowed to proceed for 10 min. at ambient temperature with gentle mixing yielding 78%±9% (n=57) $^{213}$Bi incorporation into the mAb. Although longer reaction times (20 min.) result in slightly higher yields of [$^{213}$Bi]Bi-CHX-A-DTPA-HuM195 (up to approximately 88%, under standard reaction conditions), more activity was lost through decay (loss of 23% after 20 min.) than was gained in higher yield (increase of 10%) (Nikula et al., 1998). The fraction of [$^{213}$Bi]Bi-CHX-A-DTPA-HuM195 construct that was found to be immunoreactive was 86%±10% (n=35).

Figure 5:
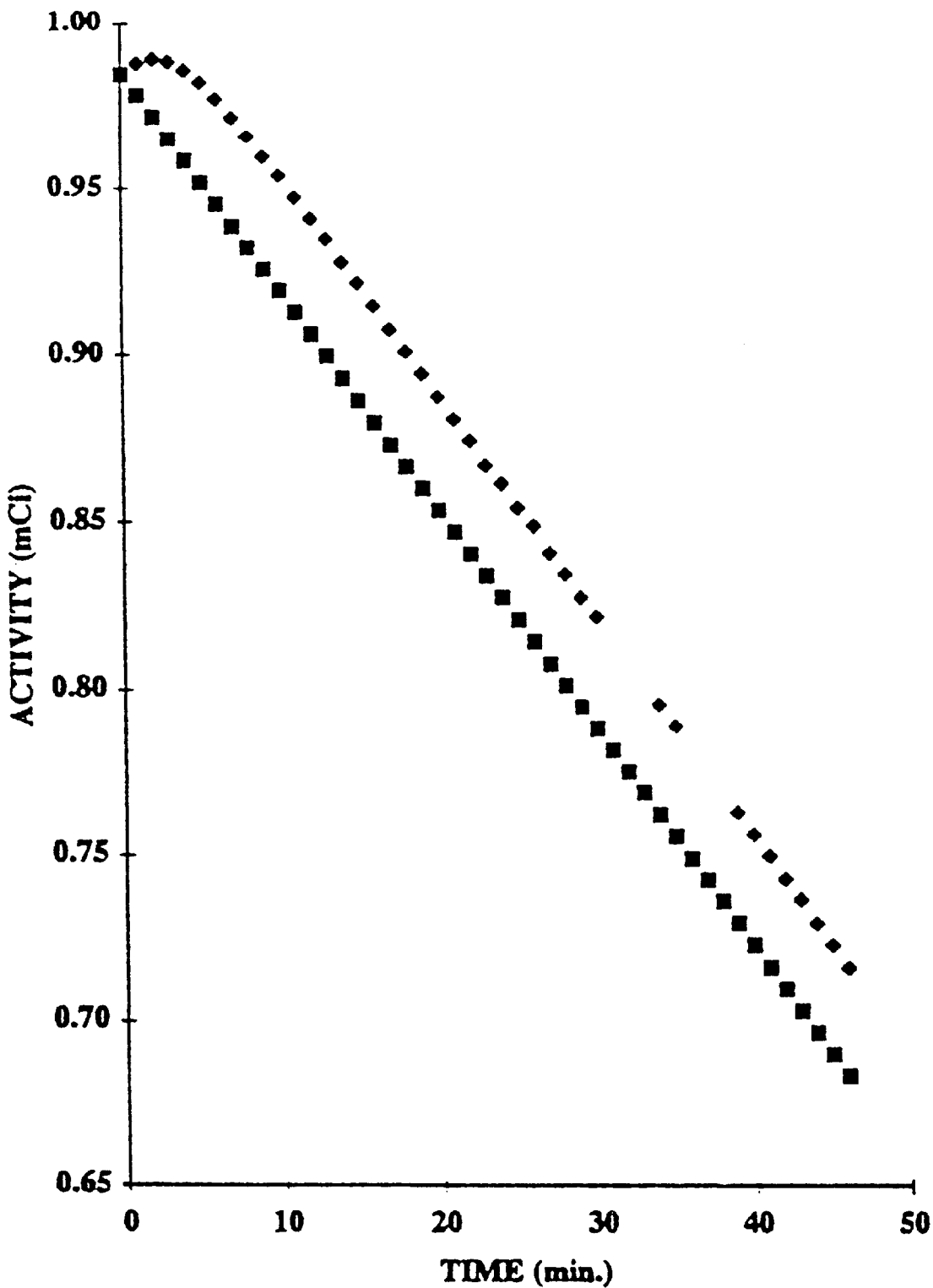
FIG. 5 shows log observed $^{213}$Bi eluate activity (diamonds) and log calculated $^{213}$Bi activity (squares) vs. time.

Francium-221 was also eluted with the $^{213}$Bi as evidenced by the characteristic decay curve exhibited by the generator eluate for a long-lived daughter, short-lived parent, no equilibrium situation (Friedlander et al., 1981). FIG. 5 is a decay plot of log observed activity of $^{213}$Bi eluate and log calculated $^{213}$Bi activity vs. time. Francium-221 possesses a 4.9 minute half-life and this radionuclide rapidly decays to $^{213}$Bi over the course of the elution, reaction, processing and delivery time so that most of the $^{221}$Fr was eliminated by the time of administration. The decay of this $^{221}$Fr contributes approximately 7.4%±0.2% more $^{213}$Bi activity in addition to the original amount of $^{213}$Bi activity originally eluted. Furthermore, extending the generator elution flow rate to approximately 0.3 ml/min. allows for the collection of an additional few percent of $^{213}$Bi activity due to the rapid regrowth of the $^{221}$Fr on the generator.

Figure 6:
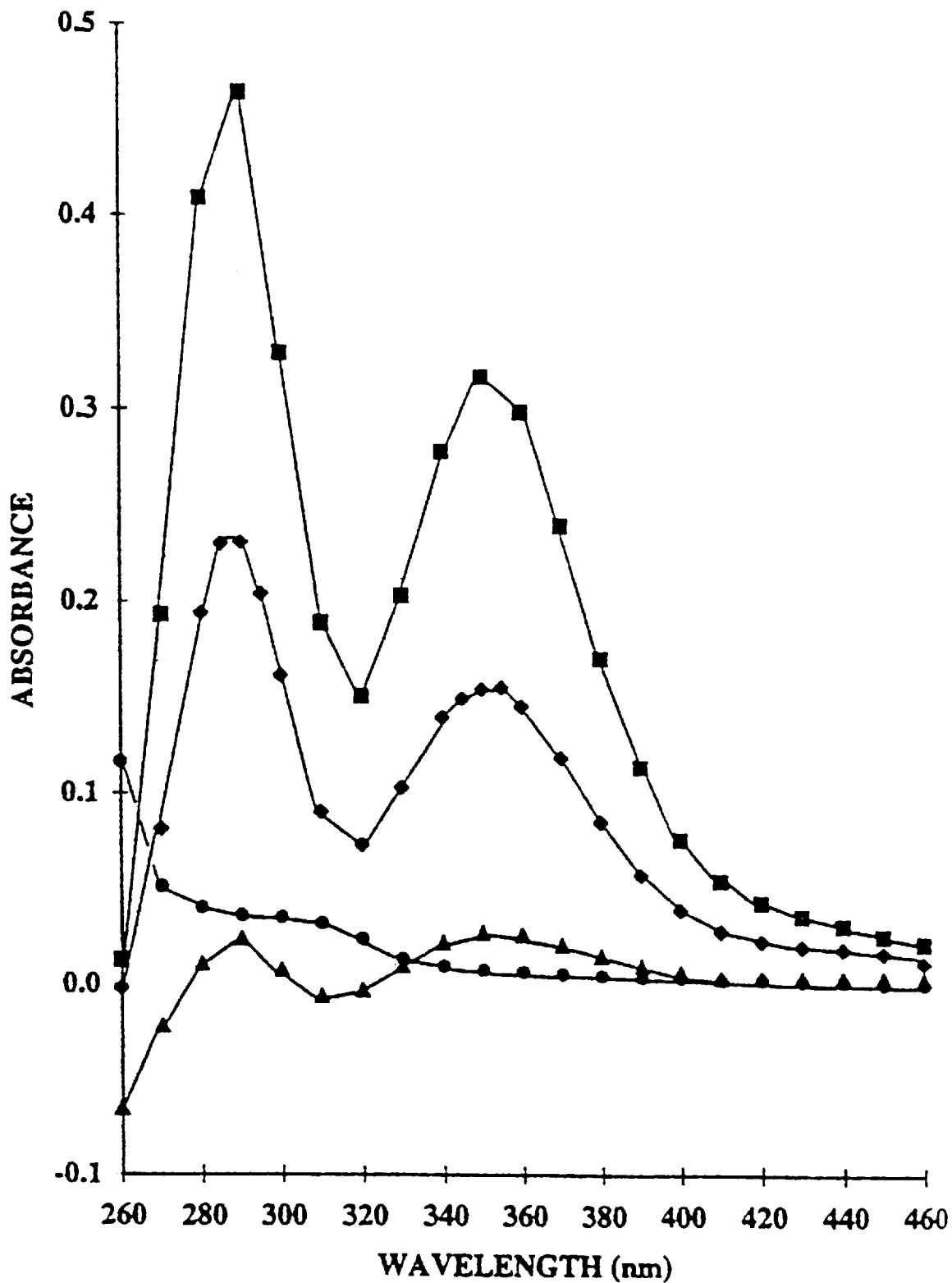
FIG. 6 shows absorption spectra of triiodide ion derived from prolonged air oxidation of a 0.1 M NaI/HCl solution (diamonds); $H_2O_2$ oxidation of a fresh 0.1 M HCl/0.1 M NaI solution (squares); elution of a fresh 0.1 M HCl/0.1 M NaI solution through a $^{213}$Bi generator (triangles); and 0.1 M NaI solution (circles). All solutions were diluted 100-fold in metal-free water for measurement.

A freshly prepared 0.1 M HCl/0.1 M NaI solution remains colorless for a short period of time at room temperature in the presence of air, but eventually will turn yellow due to oxidation of the I$^-$ ion in acidic solution to the I$_3^-$ ion by dissolved O$_2$ (Sigalla and Herbo, 1957). The elution of a fresh (colorless) acidic iodide solution through a multiple millicurie $^{213}$Bi generator also yields a yellow colored solution. The absorption spectrum of the I$_3^-$ ion (Awtrey and Connick, 1951) was observed in both the acidic air oxidized iodide solution (FIG. 6, diamonds) and the generator eluate (FIG. 6, triangles). The oxidizing effect of ionizing radiation on I$^-$ ions is a known phenomenon (Murfin, 1959). The I$_3^-$ ion absorption spectrum could also be obtained by the addition of a 0.09% H$_2$O$_2$ solution to a fresh (colorless) acidic iodide solution (FIG. 6, squares). The addition of l-ascorbic acid (final solution concentration of approximately 5 g/l) decolorizes all of these yellow solutions, presumably by reducing the I$_3^-$ ion and shifting the equilibrium of the reaction towards the I$^-$ ion.

Multiple generators were constructed and linked in series in an effort to demonstrate the feasibility of devising generators in excess of one hundred millicuries of $^{225}$Ac. There were no remarkable differences in elution and recovery of $^{213}$Bi or breakthrough of $^{225}$Ac relative to that of the standard sized generator. All indications point to the ability to construct generators in excess of 100 mCi as soon as this amount of $^{225}$Ac radionuclide becomes available without alterations in the radiolabeling conditions for the monoclonal antibody radiopharmaceuticals.

In conclusion, applying the principles outlined above allows the construction of large alpha-particle emitting radionuclide generators (e.g. 100 mCi generators) utilizing organic resin supports to prepare $^{213}$Bi radiolabeled antibody constructs for clinical application. Radioprotecting agents such as l-ascorbic acid are necessary to ensure reproducibly high recovery yields of radiolabeled product during the purification step. Breakthrough and recovery of $^{225}$Ac can be readily managed by employing an independent "catch plug" cartridge appended to the exit end of the generator or alternatively, increasing the intrinsic "catch plug" associated with each generator.

EXAMPLE 9

An Improved Clinical Labeling Procedure for the Alpha Emitting Radiometal Bi-213

Figure 7A:
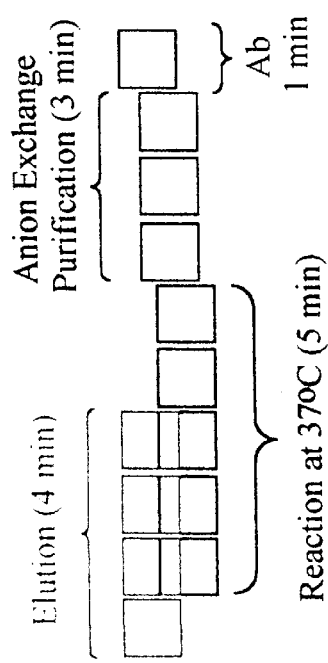
FIG. 7A is the time line for standard antibody labeling and purification procedure.

In the field of radioimmunotherapy, that is, treating human disease by use of radioisotopes targeted to specific sites or tissues with an immune protein, antibody or small molecule, there is a need to have a method to prepare short-lived, potent radiopharmaceuticals suitable for widespread human use. This is particularly true in the field of alpha particle radioimmunotherapy which uses Bi-213, an isotope with a 46 minutes half-life. The processing time for above discussed labeling and size exclusion purification method is more than 25 minutes (see FIG. 7A for the time line for standard labeling procedure). Due to a 46-min half-life of Bi-213, there is significant decay during the 25 minutes of processing, and 20–30% of drug is lost. Improvements to shorten the processing time while at the same time making a process that is reproducible and maintains the integrity of the generator and drug product is necessary for widespread use of the drug.

Figure 7B:
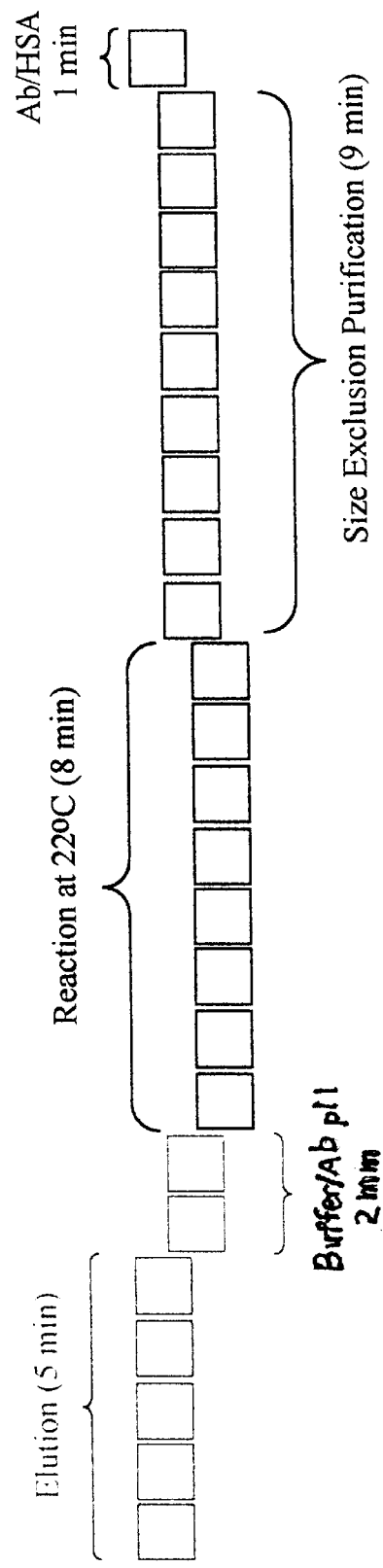
FIG. 7B is the time line for improved antibody labeling and purification procedure.

The labeling and purification procedure was modified with the following five improvements resulting in markedly reduced preparation time and increased stability of the product: 1) combine antibody with 3 N NH4Ac and directly elute Bi-213 into the antibody solution; 2) add l-ascorbic acid into 0.1 N NaI/HCl solution as eluate; 3) warm the generator and reaction tube under 37° C. and allow reaction for 2 minutes; 4) mix EDTA (or other chelates) and HSA as a quench solution; 5) anion exchange purification. The processing time after implementing all the modifications was about 10 minutes (see FIG. 7B for the time line for improved labeling procedure). Oxidation of the product and generator was reduced as well. The improvements lead to reduced time of processing, and thus less decay of the drug activity. Less decay means more isotope available per elution (dose), therefore more patients can be treated. The following describes the improvements and the experimental method for each step:

Improvement #1: Preparing the antibody directly in the neutralizing buffer, and assessing the stability of CHX-A-DTPA-HuM195 in 3 N NH4Ac. The goal is to mix monoclonal antibody with 3 N NH4Ac for long term storage without loss of its reactivity and immunoreactivity. Such modification provides the advantage of simplifying labeling procedure by combining at least two steps (adding NH4Ac and adding HuM195) into one, on which a simple kit for human use of Bismuth labeled antibodies can be based.

In detail, CHX-A-DTPA-HuM195 (0.094 ml, 10.6 mg/ml) was added into 1 ml of 3 N NH4Ac and stored in a refrigerator (2–4° C.). Labeling tests were performed with three different radiometals on day 13 (two weeks), with Bi-213; day 20 (three weeks), with Y-90; day 61 (two months) with In-111. The results are summarized in Table 1. The results show that CHX-A-DTPA-HuM195 in 3 N NH4Ac after two months still retains ability to chelate In-111 without losing its immunoreactivity. Hence, it is possible to make a stable kit with all the ingredients needed for the reaction for storage.

TABLE 1

HuM195 Stability in 3N NH4Ac and Labeling Test with Bi-213, In-111, and Y-90

| Test No | Day After | Isotope Used | Reaction Code | Activity | Antibody | DTPA to Metal Ratio |
|---|---|---|---|---|---|---|
| 1 | 13 | Bi-213 | R8.090398 | 5.14 mCi | 0.228 mg | 1183 |
| 2 | 20 | Y-90 | R1.091098 | 7.64 mCi | 0.228 mg | 10 |
| 3 | 61 | In-111 | R2.102198 | 3.29 mCi | 0.228 mg | 22 |

TABLE 1-continued

HuM195 Stability in 3N NH4Ac and Labeling Test with Bi-213, In-111, and Y-90

| Test No | Reaction Yield ITLC | Reaction Yield HPLC | Purified Product ITLC | Purified Product HPLC | ImmunoReactivity AL67 | ImmunoReactivity Control |
|---|---|---|---|---|---|---|
| 1 | 85% | 84% | 96% | ~100% | NA | NA |
| 2 | 85% | 80% | 96% | ~100% | 86.30% | 3.5% LNCAP |
| 3 | 87% | 86% | 98% | ~100% | 96.2% | 14.8% RAJI |

Improvement #2: Elimination of oxidants by elution of Bi-213 from the Ac-225 generator using a 0.1 N NaI/HCl mixed with l-Ascorbic acid solution as eluent. Significant oxidation of the generator column and the elution buffers occurs due to the extraordinary radiation flux. Up to 3 billion rad are generated in the column. Eluents are oxidized and yellowed upon retrieval from the column. One solution to this problem is to mix l-ascorbic acid (an antioxidant) with 0.1 N NaI/HCl solution for elution; there are concerns that complicated oxidation-reduction reactions could occur inside the column that would prevent routine functioning of the generator. However, addition of 100 ul of l-ascorbic acid (150 g/l, demetalized) into 3 ml of 0.1 N NaI/HCl as eluent demonstrated appropriate elutions of Bi-213 (Table 2). A freshly prepared 0.1 N NaI/HCl solution is colorless, however, after passage over the Ac-225 generator, it elutes as a yellow colored solution due to the production of $I_3^-$ ion. When the l-ascorbic acid step was added, colorless solutions were eluted off the generator indicating that l-ascorbic acid acts as a reducing agent to keep iodine in the $I^-$ form under alpha particle irradiation. The test labeling of Bi-213 eluted using l-ascorbic acid incorporated eluent with CHX-A-DTPA-HuM195 results in a 80% reaction yield which is the typical yield using only 0.1 N NaI/HCl as eluent and adding the l-ascorbic acid after elution and buffering.

TABLE 2

Ac-225/Bi-213 Generator Elution Using 0.1N NaI/HCl Mixed with l-Ascorbic Acid

| Preparation Code | Generator Activity | Bi Activity Eluted | Bi Recovered (%) | Physical Appearance | Labeling Yield |
|---|---|---|---|---|---|
| E8 (Dec. 7, 1998) | 5.10 | 2.39 | 94 | colorless | NA |
| E9 (Dec. 8, 1998) | 4.99 | 2.58 | 104 | colorless | NA |
| R10 (Dec. 9, 1998) | 4.52 | 2.37 | 105 | colorless | 80% |

As mentioned above, a freshly prepared 0.1N NaI/HCl solution is colorless. However, prolonged air oxidation of a 0.1N NaI/HCl solution also oxidizes and yellows. As a consequence, the generator needs to be eluted with a freshly prepared 0.1 N NaI/HCl (by mixing equal volumes of 0.2 N NaI and 0.2 N HCl solutions). L-ascorbic acid will prevent 0.1 N NaI/HCl solution from yellowing for at least four weeks. Because the addition of l-ascorbic acid can improve properties of NaI/HCl solution for a month, it is not necessary to prepare a fresh 0.1 N NaI/HCl for each elution. This may allow the generator operation to be robotic in the future.

Improvement #3: Markedly decrease reaction times by running the reaction at 37° C. compared to 22° C. The current published reaction method is conducted at room temperature for 8 to 10 minutes. Due to the short half-life of Bi-213, this results in a significant loss of isotope. If the reaction time can be shortened from 8–10 minutes to 1–3 minutes, it may avoid a loss of 10% of the activity of the drug due to decay.

Figure 8:
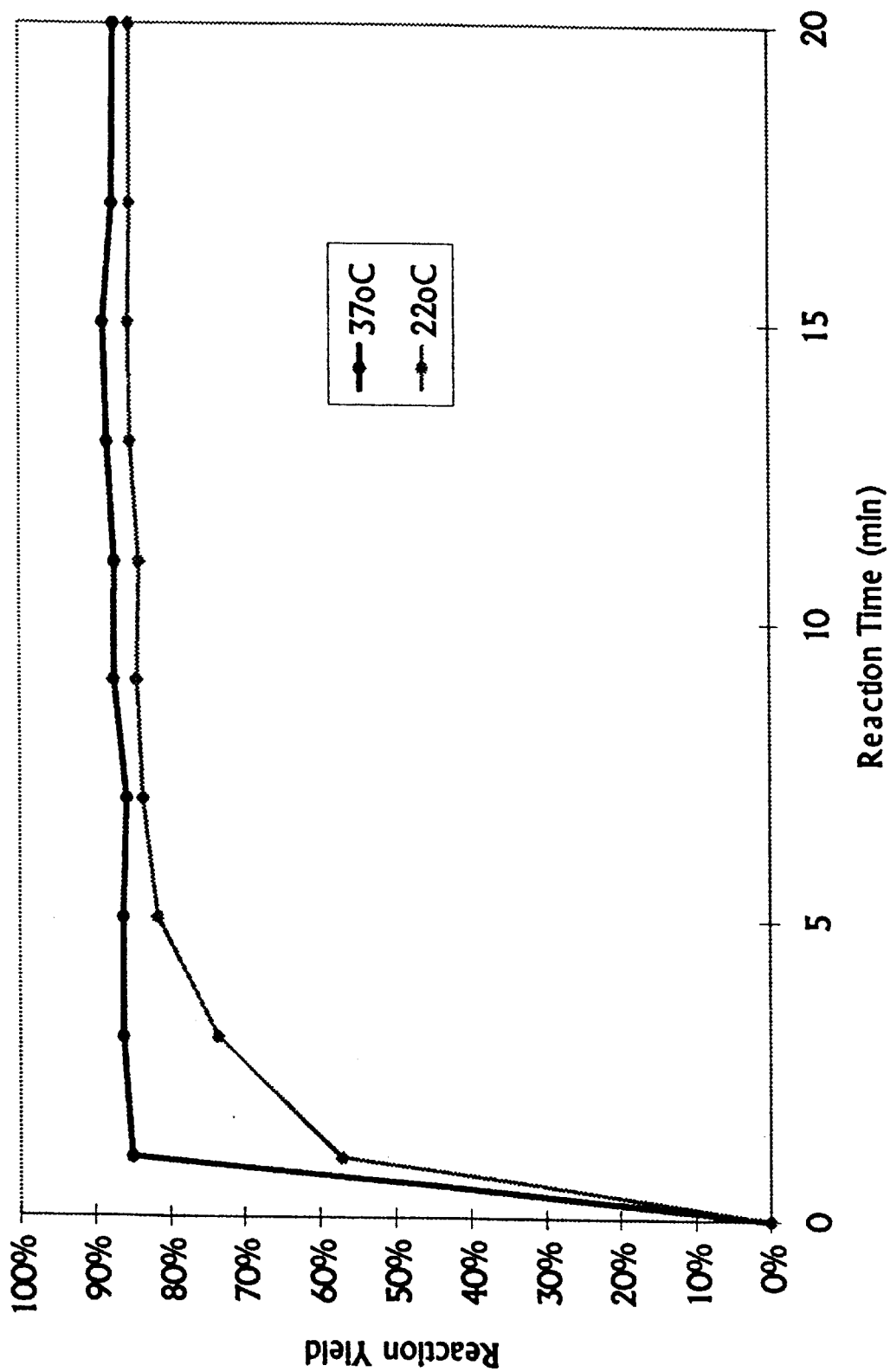
FIG. 8 shows reaction rate at different temperatures (acetate buffer pH=4.5) demonstrating that running the reaction at 37° C. may avoid a loss of 10% of the drug activity due to decay compared to 22° C.
Figure 9:
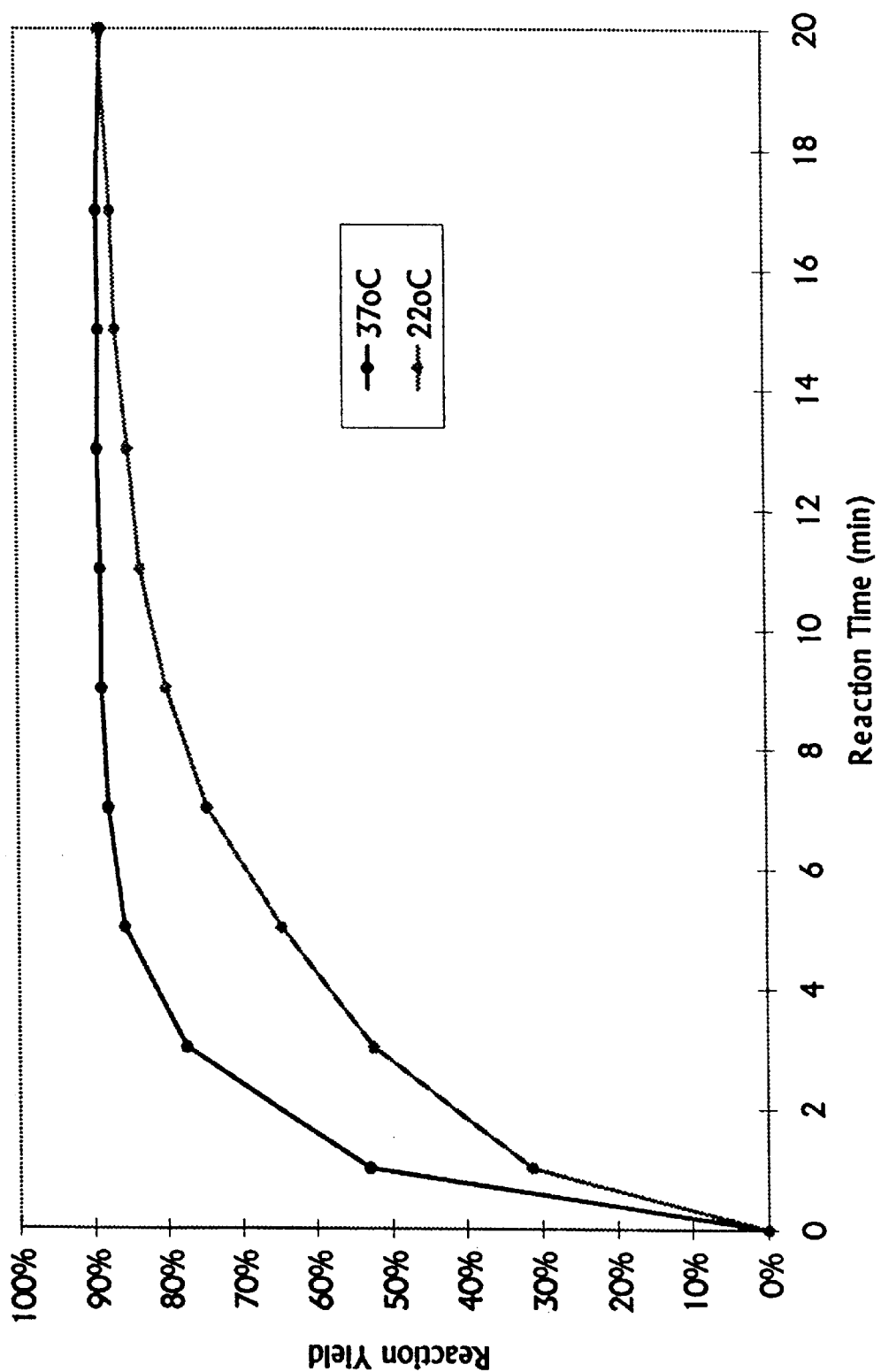
FIG. 9 shows reaction rate at different temperatures (citrate buffer pH=6) demonstrating a similar temperature dependent pattern of the reaction rate when citrate was used as buffer at pH=6.

In detail, the Bi-213 solution was warmed up to ~37° C. in a water bath or a heating unit and then CHX-A-DTPA-HuM195 was added for reaction. The kinetics of the reaction was monitored by taking aliquots of the reaction sample at different times. The reaction yield was determined using the ITLC (EDTA) method. The reaction yield vs. time was plotted compared to the reaction at room temperature (FIG. 8). The earliest data point taken was at 1 min. It was shown that the reaction went to completion at 1 min at 37° C. with ~85% yield and at 5–7 min at room temperature with ~82% yield. Although increasing the temperature does not increase the reaction yield, the reaction rate has been significantly accelerated. A similar temperature dependent pattern of the reaction rate was observed when citrate was used as buffer at pH=6 (FIG. 9).

As mentioned above, the experiment was conducted at 37° C. by preheating a Bi-213 solution to 37° C. and then adding antibody construct for reaction. However, the same reaction conditions may not allow preheating of the Bi-213 solution after elution. Therefore, other possibilities are to heat up either the 0.1 N NaI/HCl/l-ascorbic acid solution before elution or Bi-213-NaI/HCl/l-ascorbic acid solution after elution. Three options have been tested to learn the efficiency of the heating: 1) NaI and HCl solutions heated separately in a water bath or a heating unit were mixed and then used to elute the column; 2) the eluent was heated by embedding the tubing between the column and the external "catch" column in a water bath; and 3) the two methods were combined. A reaction tube with a thermometer inside was placed in a water bath and used to collect eluent. Heating the column and the reaction tube together is another possibility.

Improvement #4: Shorten reaction times by using EDTA mixed with HSA as a quench solution. An EDTA solution was added to chelate any reactive free Bi-213 and Bi-213 which was non-specifically bound on the antibody. Free radiometal may be extremely dangerous upon infusion into the patient. Anion exchange purification (discussed later) will be used to separate Bi-213-EDTA from the radiometal chelated conjugated antibody solution. Anion exchange purification requires mixing HSA with quenched Bi-213 antibody solution before loading onto the column.

It was investigated whether EDTA can be mixed with HSA as a quench solution. Since HSA solution contains some metal ions (such as Fe, Zn, and Cu), it will consume EDTA. Hence, the question is how much is EDTA needed to accomplish its function as a chasing agent. Different concentrations of EDTA in HSA solutions have been prepared by adding 20 µl of 10 mM EDTA, 100 µl of 10 mM EDTA, and 100 µl of 100 mM EDTA into 1 ml of 5% HSA to make 0.2, 2, and 20 mM EDTA-HSA solutions, respectively. Indium-111 in 0.05 M HCl (NEN) was buffered to pH 4.5 using 3 N NH4Ac. The buffered In-111 solution was mixed with EDTA-HSA solutions containing 0, 0.2, 2, 20 mM EDTA. Aliquots of each sample, including buffered In-111 stock solution, were analyzed using the ITLC method to determine the percentage of free In-Ill and In-111-EDTA complex. The results are shown in Table 3.

TABLE 3

Mixing EDTA and HSA as a Quench Solution

| Exp. No | In-111 Mixed with | EDTA Concentration | In-111 at origin ITLC (NaOH) |
|---|---|---|---|
| 1 | Nothing | 0 mM | 95 |
| 2 | HSA | 0 mM | 95 |
| 3 | EDTA-HSA | 0.2 mM | 0 |
| 4 | EDTA-HSA | 2 mM | 0.3 |
| 5 | EDTA-HSA | 20 mM | 0 |

It shows that without EDTA (Exp. 1 and 2), 95% of In-111 remained immobile at the origin in NaOH-ITLC. However, most of In-111 moved at the solvent front when EDTA added into HSA at all three concentrations of EDTA (from 0.2 to 20 mM, Exp. 3, 4, and 5). This indicates that EDTA even at 0.2 mM concentration can still efficiently chelate In-111 in present of 5% HSA.

Improvement #5: Rapid separation of the drug product by anion exchange purification. The current size exclusion purification method takes 6 to 10 minutes, which accounts for a 15 % loss of Bi-213 activity due to decay. A simple and fast anion exchange purification technique has been developed to reduce the purification time and simplify the operation. The objective is to convert Bi-213 impurities into anionic species, which can be quantitatively retained on an anion exchange column, and to refine conditions to allow antibody construct to pass through the column quantitatively without denaturing the IgG. When quenched Bi-213 antibody solution is mixed with human serum albumin (HSA, 1–5%) in isotonic saline, the AG1X8 resin in acetate form adsorbs the Bi-213 impurity and allows quantitative Bi-213 antibody elution (Table 4).

TABLE 4

Comparison of Different Concentrations of HSA

| HSA (%) | Activity Eluted (%) | Product Purity (%) | Antibody Recovery (%) | Impurity Eluted (%) |
|---|---|---|---|---|
| 0.5 | 63.3 | 95.9 | 76.3 | 2.6 |
| 2.5 | 71.7 | 96.3 | 86.8 | 2.6 |
| 0.5 wash added | 74.5 | 97.0 | 90.8 | 2.2 |
| 2.5 wash added | 81.9 | 96.5 | 99.3 | 2.8 |

The reaction was quenched with DTPA and yield was 80%. Sample of 3 ml (1.5 ml $^{213}$Bi+1.5 ml HSA) was loaded onto the column and collected (rows 1 and 2) and followed with a 3 ml wash (rows 3 and 4).

Thus, a rapid anion exchange purification method can be developed and can provide immunoreactive Bi-213 labeled antibody product with >95% purity and >95% antibody recovery. It was also demonstrated that HSA washes of the anion exchange column yields higher recovery. The procedure can be accomplished in less than 3 minutes. The technique can be reproducibly used by non-technical staff.

Figure 10:
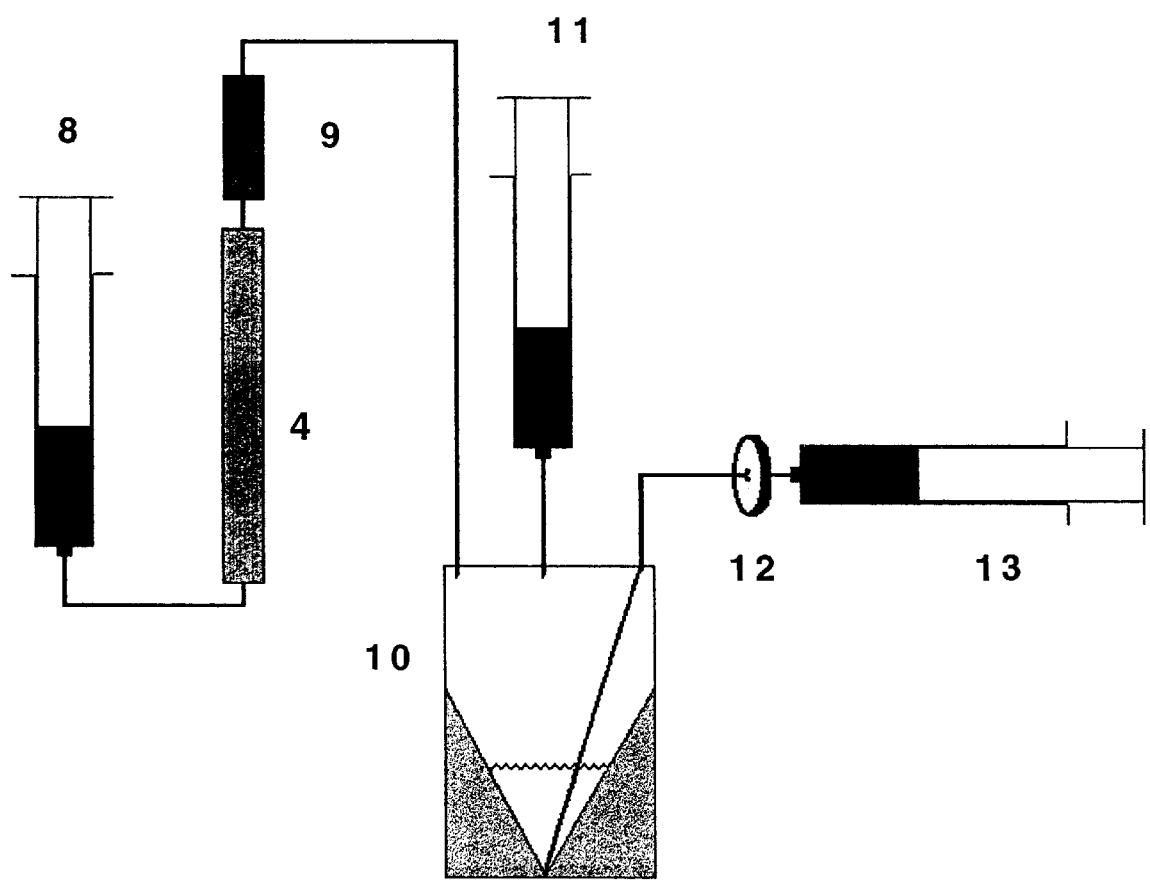
FIG. 10 is a schematic drawing of the improved radionuclide labeling and purification system 7, comprising a syringe 8 with HCl, NaI, ascorbic acid; $^{225}$Ac/$^{213}$Bi generator 4, a breakthrough purification cartridge 9, a reaction v-vial 10 with mAb and acetate, a syringe 11 with EDTA and HSA, an anion exchange disc filter (or a column) 12, and a syringe 13 to collect final product.

In conclusion, the improved radionuclide labeling and purification system 7 comprises a syringe 8 with HCl, NaI, ascorbic acid; $^{225}$Ac/$^{213}$Bi generator column 4, a breakthrough purification cartridge 9, a reaction v-vial 10 with mAb and acetate, a syringe 11 with EDTA and HSA, an anion exchange disc filter (or a column) 12, and a syringe 13 to collect final product (FIG. 10). This system can also be used for labeling and purifying non generator produced radionuclides, e.g., Y-90, In-111, etc.

EXAMPLE 10

Clinical Use of Generator Produced 213-Bismuth HuM195 Ligand

A clinical experiment (protocol) describing one possible use of an alpha emitting targeted construct follows. This experiment describes the use of the HuM195 IgG1 to target Bismuth-213 to leukemia cells and demonstrates that the constructs are stable, will deliver the isotope to the cells in a human, and will kill leukemia cells without apparent toxicity to non target tissues. Such a scheme might be used with another alpha emitter, such as Bismuth-212 attached stably to this or another ligand, such as an antibody or fragment, cytokine, or receptor ligand, each of which is capable of specific and high affinity binding to a target cell or tissue. Moreover, such ligands might be used to selectively kill nonmalignant targets such as lymphoid cell involved in a pathological process such as inflammation or autoimmunity.

Acute myelogenous leukemia (AML) is the predominant type of acute leukemia in adults. While most patients are able to achieve a complete remission with chemotherapy consisting of cytosine arabinoside and an anthracycline, prolonged disease-free survival is less than 20%. Reinduction attempts will produce second remissions in only 20–25% of patients, frequently lasting less than 6 months. Less than 5% of relapsed patients will survive one year (Stone et al., 1993).

Chronic myeloid leukemia (CML) is a biphasic disorder of early hematopoietic progenitors. The chronic phase (with a median duration of 4 years) is associated with marked elevations of mature and maturing leukocytes and leads invariably to a blastic phase resembling acute leukemia. Treatment with α-interferon has been shown to eradicate evidence of the Philadelphia chromosome by cytogenetic analysis in a minority of patients. Treatment with conventional chemotherapy, however, has had no impact on the natural history of this disease. Allogeneic bone marrow transplantation is the only potentially curative option for these patients. Since patients in accelerated or blastic phases of CML generally do not benefit from transplantation, efforts have been made to transplant these patients during the early chronic phase of their disease (Kantarjian et al., 1993).

Classified as a myelodysplastic syndrome, chronic myelomonocytic leukemia (CMMOL) is defined by the presence of a monocyte count of greater than 1 H 109/1, monocytosis of the bone marrow, anemia, and thrombocytopenia. Survival ranges from several weeks to years, with a median survival of 30 to 41 months. Treatment is mostly palliative; hydroxyurea can be used to control high peripheral blood leukocyte counts (List et al., 1990)

HuM195: A fully humanized M195 construct that has improved biochemical and immunological activities. Complementarity-determining region (CDR)-grafted humanized M195, retaining only the CDRs and other sterically important amino acids from mouse M195 were constructed using human IgG1 frameworks. Sp2/0 mouse myeloma cell lines secreting humanized M195 were grown in vitro and the antibodies were purified on PA-Sepharose by affinity chromatography using sequential pH step elutions. Purity was determined on SDS-polyacrylamide gels stained with Coomassie brilliant blue (Co et al., 1992).

The humanized M195 (HuM195) construct maintained binding specificity confirmed against a panel of CD33+ and CD33– cell lines by radioimmunoassays. Specificity for fresh hematopoietic samples from 47 patients was confirmed using a direct fluorescein conjugate of HuM195. Direct radiobinding assays showed the ability of HuM195 to be internalized rapidly after binding to the cell surface. HuM195 showed up to an 8.6-fold higher binding avidity than the original mouse M195. HuM195 is effective in inducing rabbit complement-mediated cytotoxicity against HL60 cells, and fibroblasts transfected with CD33 genes. Unlike mouse M195, HuM195 demonstrated the ability to induce antibody-dependent cell-mediated cytotoxicity (ADCC) using human peripheral blood mononuclear cells as effectors. ADCC was enhanced by the addition of IL-2 (Caron et al., 1993).

With the use of HuM195, the problem of immunogenicity can largely be eliminated. Potentially, unconjugated HuM195 may have activity in the setting of minimal residual disease where effector cell populations are present, and clinical trials are now underway to evaluate the utility of this agent in the post-remission setting. Unconjugated HuM195, however, is unlikely to have significant activity in patients with overt leukemia because of the lack of effector cells. Therefore, a less toxic M195 construct that does not require marrow transplantation is warranted.

Alpha particle emitting constructs of HuM195: Due to the high linear energy transfer and short (10–80 μm) range of alpha particles, alpha emitter-labeled antibodies are highly efficient in killing tumor cells or small tumor cell clusters, but no monoclonal antibodies (mAbs) labeled with alpha-particle emitters have been used in humans. Bismuth has two potentially useful alpha-emitting isotopes, $^{212}$Bi and $^{213}$Bi, which have half-lives of 61 and 46 minutes, respectively. Both $^{212}$Bi and $^{213}$Bi-generator systems yield high purity isotopes capable of chelation to monoclonal antibodies. In an experimental system, approximately 25 cell-bound α-particle-emitting immunoconjugates per target cell and four α-particle traversals through the nucleus were required to reduce clonogenic survival of a lymphoma cell line by 90% (Macklis et al., 1992). Specific cytotoxicity of $^{212}$Bi-labeled anti-Tac (anti-CD25) monoclonal antibody has been demonstrated against an adult T-cell leukemia line in vitro (Kozak et al., 1986). In previous studies, mice inoculated intraperitoneally with the murine tumor line EL-4 were cured of their ascites after intraperitoneal injection of 150 μCi of a $^{212}$Bi-labeled antibody conjugate. Animals receiving over 400 μCi of $^{212}$Bi showed signs of radiation exposure such as weight loss, diarrhea, and infection (Macklis et al., 1988). Additionally, in vivo specificity and efficacy of radioimmunotherapy with $^{212}$Bi and $^{211}$At have been seen in murine erythroleukemia and neoplastic meningitis models, respectively (Huneke et al., 1992)

Alpha emitters have now been conjugated via a bifunctional chelate (CHX-A-DTPA) to HuM195 with high efficiency (>90%) and high specific activities (up to 20 mCi/mg). This chelator had a high avidity for radiometals and lack of immunogenic responses in experimental animals (Camera et al., 1994). $^{111}$In-, $^{206}$Bi-, $^{212}$Bi-, and $^{213}$Bi-HuM195 constructs have been made. The immunoreactivity of chelated HuM 195 (HuM 195-CHX-A-DTPA) varied from 80 to 95%. HuM195-CHX-A-DTPA was rapidly internalized into cells. In vitro cell killing experiments with different specific activities of $^{212}$Bi-HuM195 showed dose-dependent and specific activity-dependent killing of HL60 target leukemia cells. $^{213}$Bi-HuM195 was injected into healthy BALB/C mice at doses of 0.5 to 20 mCi/kg. No changes in weight, viability, hemoglobin, or leukocyte count were seen. At doses of 70 mCi/kg, two of three mice died within two weeks and a third showed significant reductions in leukocyte counts. The doses planned in this clinical trial range from 0.28 to 0.7 mCi/kg. Mathematical modeling predicted the red marrow dose from $^{213}$Bi to be 0.55 mGy/MBq or 1.5 mSv/MBq. The percentage of tumor cells killed for 10 gm or less of single isolated cells was >99.9% and approximately 50% for 100 gm of disease when 370 MBq (10 mCi) of $^{213}$Bi were administered.

Clinical grade $^{213}$Bi generators capable of producing 25–50 mCi will be prepared. Actinium is supplied dried onto a glass ampule from the Transuranium Elements Institute in Karlsruhe, Germany. $^{213}$Bi is eluted from the generator and chelated to HuM195-CHX-A-DTPA, followed by separation of $^{213}$Bi-HuM195 by size exclusion chromatography. Sensors for OD280 and (emissions will be used to determine yield and specific activity. Unlabeled HuM195 may be added to adjust the dose as necessary. This will be performed at Sloan-Kettering Institute immediately prior to injection into patients. $^{213}$Bi-HuM195 will be diluted in normal saline with 1% human serum albumin (HSA) to a total volume of 10 ml for injection.

Patients will be treated in the Nuclear Medicine Department on either an outpatient or inpatient basis. Given the short-half life of $^{213}$Bi, radiation exposure to hospital staff will be minimal and radiation isolation for patients is not required. Patients will be monitored by a Radiation Safety Officer and instructed in the proper disposal of waste. Additionally, patients will not be discharged for two to three hours after infusion, by which time any remaining gamma radiation will be trivial. Patients will receive $^{213}$Bi-Hum195 by IV push over 5 minutes twice daily, 5–8 hours apart, according to the dose escalation scheme below:

Dose Level 1 (0.28 mCi/kg):
  Day 1: 0.07 mCi/kg BID
  Day 2: 0.07 mCi/kg BID
Dose Level 2 (0.42 mCi/kg):
  Day 1: 0.07 mCi/kg BID
  Day 2: 0.07 mCi/kg BID
  Day 3: 0.07 mCi/kg BID
Dose Level 3 (0.56 mCi/kg):
  (4 days as above)
Dose Level 4 (0.7 mCi/kg):
  (5 days as above)

Because of the short half-life of $^{213}$Bi, individual doses of $^{213}$Bi may vary by 20%. Efforts will be made to keep the cumulative dose as planned by adjusting subsequent doses. At least three patients will be treated at each dose level according to the dose escalation scheme. If acceptable toxicity is encountered, patients at the next dose level will be enrolled.

Eleven patients have entered on four dose levels. More than 50 doses of the drug were synthesized according to the specifications and injected into the patients. Doses could be prepared from the generator at least every 3–4 hours. The generator provided drug that met specifications for at least nine days allowing the treatment of patients. Real time pharmacokinetics were assessed by gamma imaging and serial blood work. The drug targeted first to the sites of leukemia and monocyte/macrophage cells in the liver and spleen. The bone marrow was targeted next. Over time, with succeeding injections, uptake into the liver decreased by 50% as sites were saturated, and uptake in the bone marrow increased by 100%, as more drug became available. The estimated radiation doses in REM to the whole body, kidneys or other non-target organs were 0.03; to the blood, 125; to the liver 600; to the spleen 1400;1 and to the red marrow, 1100. Target to non-target dose ratios were therefore 25,0000–50,000 to one. There was no acute toxicity in any patient. There was no extramedullary toxicity seen in any patient. In most patients, peripheral blood cell counts (leukemia blasts and white cells) began to fall within 48 hours after treatment and were reduced by up to 90%. Counts usually returned within two weeks. The bone marrow at one week showed reduced cellularity and reduced leukemia blast percentages in the majority of patients (up to 70% reduced).

Conclusion from initial levels: The drug can be prepared and administered safely and repeatedly without extramedullary toxicity. The drug displayed pharmacokinetics consistent with rapid, specific, and stable targeting only to appropriate cancer cell sites. Significant anti-leukemic activity was seen even at the lowest level. Dose escalation will continue.

In conclusion, a generator capable of producing multiple high levels of Bismuth for labeling of clinically useful ligands (or antibodies) is described. This generator conforms to the essential physical requirements (yield of product and radiochemical and radionuclidic purity) outlined in (Knapp et al., 1984 ).

The following references may have been cited herein:
Atcher, et al., (1988) *Appl. Radiat. Isot.* 39, 283.
Awtrey, et al., (1951) *J.Am.Chem.Soc.* 73, 1842.
Boll, et al., (1997) *J. Label. Compds. and Radiopharm.* 40, 341.
Camera, et al., (1994) *J Nucl Med* 35: 882–889.
Caron, et al., (1992) *Cancer Res.* 52, 6761.
Caron, et al., (1994) *Blood* 83:1760–1768.
Chang, (1996) http://necs01.dne.bnl.gov/CoN/index.html.
Co, et al., (1992) *J Immunol.* 148:1149–1154.
Finn, et al., (1997) *J. Label. Compds. and Radiopharm.* 40, 293.
Friedlander, et al., (1981) *Nuclear and Radiochemistry*, Third Edition. John Wiley & Sons, New York.
Gangwer, et al., (1977) *Radiation Effects on Ion Exchange Materials.* BNL 50781.
Geerlings, et al., (1993) *Nucl. Med. Comm.* 14, 121.
Huneke, et al., (1992) *Cancer Res* 52: 5818–5820.
Jurcic, et al., (1997) *Blood* 90(suppl), 504a.
Knapp, et al., eds, *Radionuclide Generators*, ACS symposium Series #241, ACS, Washington, D.C., 1984, p185.
Kozak, et al., (1986) *Proc Natl Acad Sci USA* 83:474–478.
Macklis, et al., (1992) *Radiation Res* 130: 220–226.
Macklis, et al. 91988) *Science* 240:1024–1026.
McDevitt, et al., (1996) *Tumor Targeting* 2(3), 182.
Murfin,(1959) *J. Inst. Sci. Techn.* 5(4), 10.
Nikula, et al., (1995) *Nucl. Med. Biol.* 22, 387.
Nikula, et al., (1998) *J. Nucl. Med.* (to be published)
Sigalla, et al., (1957) *J. Chim. Phys.* 54, 733.
Spivakov, et al., (1979) *J. Inorg. Nucl. Chem.* 41, 453.
Van Geel, et al., (1994) European Patent nb. 0 443 479 B1.
Van Geel, (1995) *ITU Annual Report* 1995-(EUR 16368)-*Basic Actinide Research* 55.
Wu, et al., (1996) *Abstracts of Papers of the American Chemical Society* 212(1), 61-NUCL.
Zalutsky, et al., (1994) *Cancer Res* 54: 4719–4725.24.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A bismuth-213 generator, comprising:
   a first container containing $^{225}$Ac solution;
   a second container;
   a generator column;
   a valve, said valve simultaneously and directly connected to an end of each of said first container, said second container and said column;
   and a third container, said third container connected to said generator column at an exit end opposite to the end connected to said valve.

2. The generator of claim 1, wherein said first container, said second container and said third container are individually a syringe or a delivery device.

3. The generator of claim 1, wherein said valve is a 3-way stopcock.

4. The generator of claim 1, wherein said second container contains a chromatographic medium, and said third container applies a negative pressure for loading said medium onto said generator column.

5. The generator of claim 4, wherein said chromatographic medium is resin.

6. The generator of claim 5, wherein said resin is equilibrated with HCl solution.

7. The generator of claim 1, further comprising a cartridge appended to the exit end of said generator column between said exit end and said third container.

8. The generator of claim 7, wherein said cartridge reduces the breakthrough of $^{225}$Ac actinium-225 eluted from said generator column.

9. A method for preparing a bismuth-213-labeled compound, comprising the steps of:
   (a) operating the bismuth-213 generator of claim 1 to load actinium-225 throughout a resin in the generator column;
   (b) eluting the generator column with an elution buffer to obtain an eluate;
   (c) adding said compound to said eluate to react;
   (d) adding a quench solution to the reaction; and
   (e) purifying the solution from (c) to obtain a final product, wherein said final product contains said bismuth-213-labeled compound.

10. The method of claim 9, wherein said elution buffer comprises a NaI/HCl solution or a NaBr/HCl solution.

11. The method of claim 10, wherein said elution buffer further comprises an antioxidant to prevent said elution buffer from oxidizing.

12. The method of claim 11, wherein said antioxidant is l-ascorbic acid.

13. The method of claim 9, wherein said compound is premixed with a neutralizing buffer.

14. The method of claim 13, wherein said neutralizing buffer is selected from the group consisting of NH$_4$Ac, Na citrate and NH$_4$ citrate.

15. The method of claim 9, wherein said reaction is run at a temperature higher than room temperature.

16. The method of claim 9, wherein said quench solution is selected from the group consisting of EDTA, DTPA, EDTMP, EDTA+human serum albumin, DTPA+human serum albumin, EDTMP+human serum albumin and a chelate.

17. The method of claim 9, wherein said method of purification is selected from the group consisting of size exclusion chromatography, ion exchange purification, reverse phase chromatography and affinity chromatography.

18. The method of claim 9, wherein said compound is selected from the group consisting of an antibody, a fragment of an antibody, a cytokine and a receptor ligand.

19. The method of claim 9, wherein processing time for completing said steps is from about 10 minutes to about 25 minutes.

20. The method of claim 9, wherein said generator column reduces the leakage of $^{225}$Ac.

21. The method of claim 9, wherein said generator column is capable of producing from about 10 mCi to about 100 mCi of Bismuth-213.

22. A system for preparing a bismuth-213-labeled compound, comprising:
   a first container,
   a generator column loaded with actinium-225 by the generator of claim 1;
   a reaction vial;
   a second container;
   purification means; and
   a third container, said third container collecting a final product, wherein said final product contains said bismuth-213-labeled compound.

23. The system of claim 22, wherein said purification means is a size exclusion column, an ion exchange column, a reverse phase column, an affinity column or a disc filter.

24. The system of claim 22, wherein said first container, said second container and said third container are individually a syringe or a delivery device.

25. The system of claim 22, wherein said first container contains an elution buffer.

26. The system of claim 25, wherein said elution buffer comprises a NaI/HCl solution or a NaBr/HCl solution.

27. The system of claim 26, wherein said elution buffer further comprises an antioxidant.

28. The system of claim 27, wherein said antioxidant is l-ascorbic acid.

29. The system of claim 22, wherein said reaction vial contains said compound premixed with a neutralizing buffer.

30. The system of claim 29, wherein said neutralizing buffer is selected from the group consisting of NH$_4$Ac, Na citrate and NH$_4$ citrate.

31. The system of claim 22, wherein said second container contains a quench solution.

32. The system of claim 31, wherein said quench solution is selected from the group consisting of EDTA, DTPA, EDTMP, EDTA+human serum albumin, DTPA+human serum albumin, EDTMP+human serum albumin and a chelator.

33. The method of claim 22, wherein said compound is selected from the group consisting of an antibody, a fragment of an antibody, a cytokine and a receptor ligand.

34. A kit for preparing a bismuth-213-labeled compound, wherein said kit comprises:
   (a) a bismuth-2 13 generator, comprising:
      a first container containing $^{225}$Ac solution;
      a second container;
      a generator column;
      a valve, said valve simultaneously and directly connected to an end of each of said first container, said second container and said column; and a third container, said third container connected to said generator column at an exit end opposite to the end connected to said valve; and (b) a fourth container to contain an eluant;
a reaction vial to contain said unlabeled compound premixed with a neutralizing buffer;
a fifth container to contain a quenching solution;
purification means; and
a sixth container, said sixth container collecting a final product, wherein said final product contains said bismuth-213-labeled compound.

35. The kit of claim 34, wherein said first container, said second container and said third container are individually a syringe, or a delivery device.

36. The kit of claim 34, wherein said valve is a 3-way stopcock.

37. The kit of claim 34, wherein said second container contains a resin and said third container applies a negative pressure for loading said resin onto said generator column.

38. The kit of claim 37, wherein said resin is equilibrated with HCl solution.

* * * * *

UNITED STATES PATENT AND TRADEMARK OFFICE
CERTIFICATE OF CORRECTION

PATENT NO. : 6,603,127 B1  Page 1 of 1
APPLICATION NO. : 09/647491
DATED : August 5, 2003
INVENTOR(S) : Scheinberg et al.

It is certified that error appears in the above-identified patent and that said Letters Patent is hereby corrected as shown below:

Insert after line 5 of Column 1, the following:

--<u>Federal Funding Legand</u>

This invention was created, in part, using funds from the federal government under National Institutes of Health Grant Nos. CA55349, CA58260 and CA33049. Consequently, the U.S. government has certain rights in this invention.--

Signed and Sealed this

Fifteenth Day of January, 2008

JON W. DUDAS
*Director of the United States Patent and Trademark Office*